United States Patent
Hall et al.

(10) Patent No.: US 9,750,253 B2
(45) Date of Patent: Sep. 5, 2017

(54) PESTICIDALLY ACTIVE SUBSTITUTED PYRIDYL CARBOXAMIDES

(71) Applicant: Syngenta Participations AG, Basel (CH)

(72) Inventors: Roger Graham Hall, Stein (CH); Andrew Edmunds, Stein (CH); Andre Jeanguenat, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/782,382

(22) PCT Filed: Apr. 3, 2014

(86) PCT No.: PCT/EP2014/056635
§ 371 (c)(1),
(2) Date: Oct. 5, 2015

(87) PCT Pub. No.: WO2014/166795
PCT Pub. Date: Oct. 16, 2014

(65) Prior Publication Data
US 2016/0050924 A1 Feb. 25, 2016

(30) Foreign Application Priority Data
Apr. 10, 2013 (EP) .................... 13163045

(51) Int. Cl.
*A01N 43/58* (2006.01)
*A01N 43/56* (2006.01)
*C07D 401/14* (2006.01)

(52) U.S. Cl.
CPC ............ *A01N 43/56* (2013.01); *A01N 43/58* (2013.01); *C07D 401/14* (2013.01)

(58) Field of Classification Search
None
See application file for complete search history.

(56) References Cited

FOREIGN PATENT DOCUMENTS

WO    WO 2009027393 A2 * 3/2009 ............. A01N 43/56
WO    2010/112177 A1    10/2010

OTHER PUBLICATIONS

Nguyen et al., International Journal of Biomedical Science (2006), pp. 85-100.*
Extended European Search Report for 13163045.1, mailed on Jun. 6, 2013.
International Search Report for International Patent Application No. PCT/EP2014/056635 mailed May 15, 2014.

* cited by examiner

*Primary Examiner* — John Pak
*Assistant Examiner* — Frank Choi
(74) *Attorney, Agent, or Firm* — R. Kody Jones

(57) ABSTRACT

Compounds of formula I wherein m is 0 or 1; Z is methine or nitrogen; X is oxygen or sulfur, $R_1$ is $C_1$-$C_6$-alkyl, halo-$C_1$-$C_6$-cycloalkyl or $C_2$-$C_6$-alkynyl; $R_2$ is $C_1$-$C_6$-alkyl, $C_1$-$C_6$-haloalkyl, $C_3$-$C_6$-cycloalkyl, halo-$C_3$-$C_6$-cycloalkyl, fluoro, chloro or bromo; $R_3$ is $C_1$-$C_3$-alkyl; $R_4$ is hydrogen, $C_1$-$C_6$-alkyl, fluoro, chloro, bromo or cyano; n is 0, 1, 2 or 3; $R_5$ is hydrogen, fluoro, chloro or bromo; and agrochemically acceptable salts and enantiomers of those compounds can be used as insecticides and can be prepared in a manner known per se.

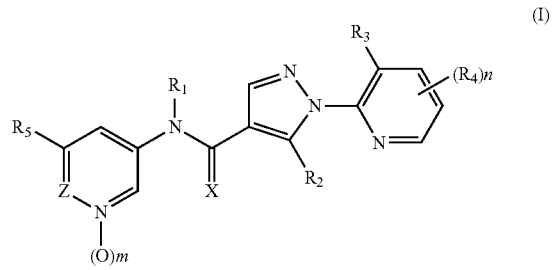

14 Claims, No Drawings

PESTICIDALLY ACTIVE SUBSTITUTED PYRIDYL CARBOXAMIDES

RELATED APPLICATION INFORMATION

This application is a 371 of International Application No. PCT/EP2014/056635, filed 3 Apr. 2014, which claims priority to EP Patent Application No. 13163045.1, filed 10 Apr. 2013, the contents of which are incorporated herein by reference herein.

The present invention relates to substituted pyridyl carboxamide derivatives, to processes for their preparation, to pesticidal, in particular insecticidal, acaricidal, molluscicidal and nematicidal compositions comprising those compounds and to their use for controlling pests such as insect, acarine, mollusc and nematodes pests.

Pesticidally active pyridyl carboxamide derivatives are known and described, for example, in WO 2009/027393 and WO 2010/112177. It has been found that novel pyridyl carboxamides with a specific substitution pattern have pesticidal properties.

The present invention accordingly relates to compounds of formula I,

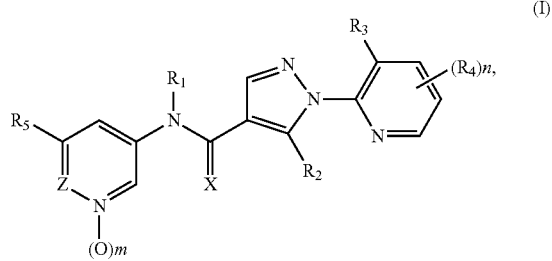

wherein,
m is 0 or 1;
Z is methine or nitrogen;
X is oxygen or sulfur,
$R_1$ is $C_1$-$C_6$-alkyl, $C_3$-$C_6$-cycloalkyl or $C_2$-$C_6$-alkynyl;
$R_2$ is $C_1$-$C_6$-alkyl, $C_1$-$C_6$-haloalkyl, $C_3$-$C_6$-cycloalkyl, halo-$C_3$-$C_6$-cycloalkyl, fluoro, chloro or bromo;
$R_3$ is $C_1$-$C_3$-alkyl;
$R_4$ is hydrogen, $C_1$-$C_6$-alkyl, fluoro, chloro, bromo or cyano;
n is 0, 1, 2 or 3;
$R_5$ is hydrogen, fluoro, chloro or bromo; and agrochemically acceptable salts and enantiomers of those compounds.

Compounds of formula I which have at least one basic centre can form, for example, acid addition salts, for example with strong inorganic acids such as mineral acids, for example perchloric acid, sulfuric acid, nitric acid, nitrose acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl and hexyl and their branched isomers. Alkynyl radicals are derived from the alkyl radicals mentioned. The alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

The cycloalkyl groups preferably have from 3 to 6 ring carbon atoms, for example cyclopropyl, cyclobutyl, cyclopentyl and cyclohexyl.

The compounds of formula I according to the invention also include hydrates which may be formed during the salt formation.

In a preferred embodiment according to the invention, Z is methine.

In another preferred embodiment according to the invention, Z is nitrogen.

In another preferred embodiment according to the invention X is oxygen.

Preferably, $R_1$ is methyl, ethyl, isopropyl, cyclopropyl, $CH_2CF_3$, or prop-2-ynyl.

Preferably, $R_2$ is methyl, ethyl, isopropyl, cyclopropyl, $CF_3$, $CF_2H$ or chloro.

Preferably, $R_3$ is methyl, ethyl or isopropyl.

In a preferred embodiment according to the invention, in compounds according to formula I,
m is 0;
Z is methine;
X is oxygen;
$R_1$ is methyl, ethyl, isopropyl, cyclopropyl, $CH_2CF_3$, or prop-2-ynyl;
$R_2$ is methyl, ethyl, isopropyl, cyclopropyl, $CF_3$, $CF_2H$ or chloro; and
$R_3$ is methyl, ethyl or isopropyl.

In another preferred embodiment according to the invention, in compounds according to formula I,
m is 0;
Z is nitrogen;
X is oxygen;
$R_1$ is methyl, ethyl, isopropyl, cyclopropyl, $CH_2CF_3$, or prop-2-ynyl;
$R_2$ is methyl, ethyl, isopropyl, cyclopropyl, $CF_3$, $CF_2H$ or chloro; and
$R_3$ is methyl, ethyl or isopropyl.

In a most preferred embodiment according to the invention, in the compounds according to formula I, m is 0;
Z is methine;
X is oxygen;
$R_1$ is methyl, ethyl or prop-2-ynyl,
$R_2$ is methyl, ethyl or isopropyl, and
$R_3$ is methyl, ethyl or isopropyl.

N-oxides of the preferred compounds above are also preferred according to the invention. The invention also specifically relates to compounds according to formula I, wherein m is 1;
Z is CH;
X is oxygen;
$R_1$ is methyl, ethyl, isopropyl, cyclopropyl, $CH_2CF_3$, or prop-2-ynyl;
$R_2$ is methyl, ethyl, isopropyl, cyclopropyl, $CF_3$, $CF_2H$ or chloro; and
$R_3$ is methyl, ethyl or isopropyl.

In all of the preferred embodiments of the invention mentioned above, $R_4$ is preferably hydrogen, halogen or cyano. Independently from this definition, in all of the preferred embodiments of the invention mentioned above, $R_5$ is preferably hydrogen or fluorine, in particular hydrogen.

An especially preferred group of compounds of formula I is represented by the compounds of formula Id

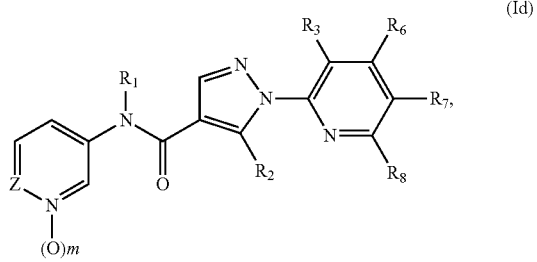

(Id)

wherein
Z is methine or nitrogen;
m is 0 or 1;
$R_1$, $R_2$ and $R_3$, independently from each other, are $C_1$-$C_6$alkyl; $R_1$ preferably methyl or ethyl and $R_2$ and $R_3$ preferably methyl;
$R_6$ is hydrogen or halogen, preferably hydrogen or chlorine;
$R_7$ is hydrogen, halogen or cyano; and
$R_8$ is hydrogen or halogen, preferably hydrogen or chlorine.

The compounds of the invention may be prepared by a variety of methods. For example, compounds of the formula I where X=O, and m=0 can be prepared by reacting an activated pyrazole carboxylic acid derivative II with a 3-amino pyridine (Z=methine) or a 3-amino pyridazine (Z=nitrogen) derivative of formula III, as shown in Scheme 1. Activated pyrazole carboxylic acid derivatives of formula II are for example halides, activated esters, or anhydrides, for example acid chlorides, para-nitrophenyl esters, N-hydroxysuccinamide esters, and hydroxybenzotriazol-1-yl esters. In Scheme 1, $R_1$, $R_2$, $R_3$, $R_4$, $R_5$, n and Z have the meanings described above, and X is a suitable leaving group such as halide, para-nitrophenoxy, etc. The reaction can optionally be performed in the presence of an acid scavenger, as required, such as a tertiary amine such as triethylamine or pyridine.

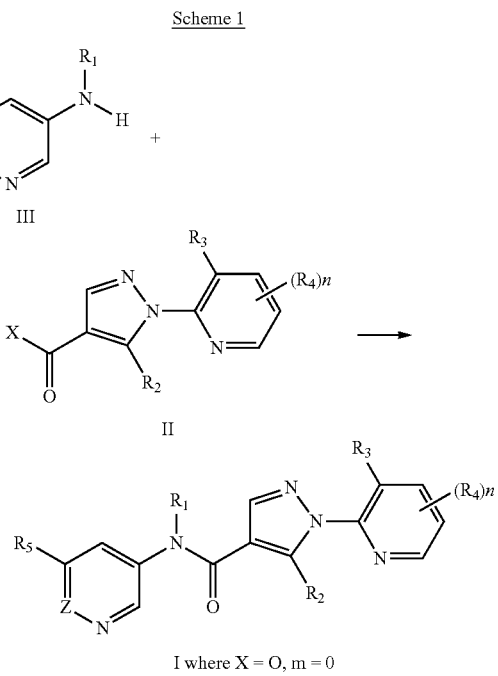

Scheme 1

I where X = O, m = 0

Compounds of the formula I where X=oxygen, and m=0 can also be prepared by reacting a pyrazole carboxylic acid derivative of formula IV with a 3-amino pyridine (Z=methine) or a 3-amino pyridazine (Z=nitrogen) derivative of formula III, in the presence of a coupling agent, as shown in Scheme 2.

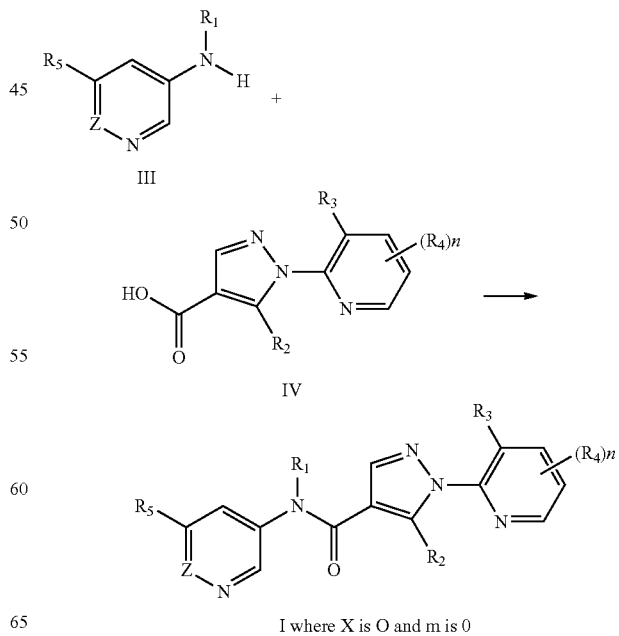

Scheme 2

I where X is O and m is 0

In Scheme 2, $R_1$, $R_2$, $R_3$, $R_4$, $R_5$, n and Z have the meanings described above.

Suitable coupling agents are, for example:

coupling agents based on carbodiimides, for example N,N'-dicyclohexylcarbodiimide [J. C. Sheehan, G. P. Hess, *J. Am. Chem. Soc.* 1955, 77, 1067], N-(3-dimethylaminopropyl)-N'-ethylcarbodiimide;

coupling agents which form mixed anhydrides with carbonic esters, for example 2-ethoxy-1-ethoxycarbonyl-1,2-dihydroquinoline [B. Belleau, G. Malek, *J. Amer. Chem. Soc.* 1968, 90, 1651], 2-isobutyloxy-1-isobutyloxycarbonyl-1,2-dihydroquinoline [Y. Kiso, H. Yajima, *J. Chem. Soc., Chem. Commun.* 1972, 942];

coupling agents based on phosphonium salts, for example (benzotriazol-1-yloxy)tris(dimethylamino)phosphonium hexafluorophosphate [B. Castro, J. R. Domoy, G. Evin, C. Selve, *Tetrahedron Lett.* 1975, 14, 1219], (benzotriazol-1-yl-oxy)tripyrrolidinophosphonium hexafluorophosphate [J. Coste et al., *Tetrahedron Lett.* 1990, 31, 205];

coupling agents based on uronium salts or having a guanidinium N-oxide structure, for example N,N,N',N'-tetramethyl-O-(1H-benzotriazol-1-yl)uronium hexafluorophos-phate [R. Knorr, A. Trzeciak, W. Bannwarth, D. Gillessen, *Tetrahedron Lett.* 1989, 30, 1927], N,N,N',N'-tetramethyl-O-(benzotriazol-1-yl) uronium tetrafluoroborate, (benzotriazol-1-yloxy)dipiperidinocarbenium hexafluorophosphate [S. Chen, J. Xu, *Tetrahedron Lett.* 1992, 33, 647];

coupling agents which form acid chlorides, for example bis-(2-oxo-oxazolidinyl)phosphinic chloride [J. Diago-Mesequer, *Synthesis* 1980, 547].

Compounds of formula I can also be prepared from compounds of formula Ia, by reacting with a suitable alkylating agent of formula V in the presence of a base, as shown in Scheme 3.

Scheme 3

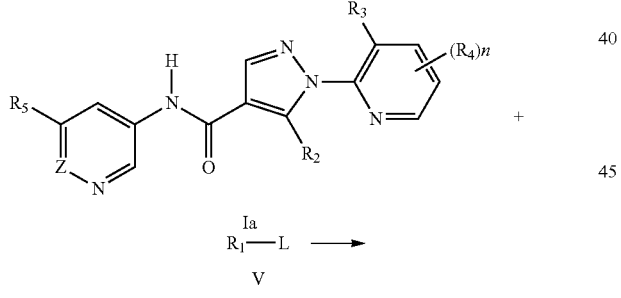

Ia
$R_1$—L
V

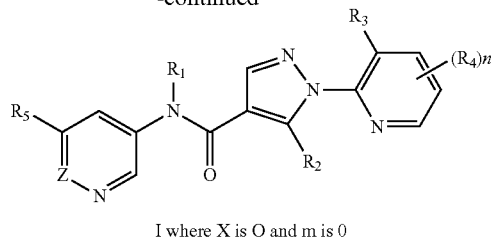

I where X is O and m is 0

In Scheme 3, $R_1$, $R_2$, $R_3$, $R_4$, $R_5$, n and Z have the meanings described above, and L is a leaving group such as halide, mesylate, tosylate, triflate, etc.

Compounds of formula I, wherein $R_1$, $R_2$, $R_3$, $R_4$, $R_5$ and n have the meanings described above, Z=CH and m=1 can be prepared from compounds of formula Ib by reacting with a suitable oxidizing agent, such as meta-chloroperbenzoic acid, sodium periodate, oxone, etc, as shown in Scheme 4.

Scheme 4

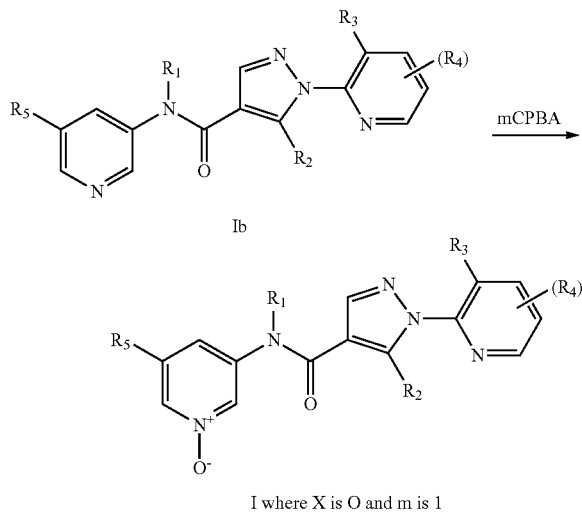

I where X is O and m is 1

Compounds of formula I where X=sulfur can be prepared from compounds of the formula Ic where X=oxygen by reacting with 2,4-bis(4-methoxyphenyl)-1,3,2,4-dithiadiphosphetane-2,4-disulfide (Lawessons reagent) or with phosphorus pentasulfide according to the method described by M. Jesberger et. al., *Synthesis*, 2003, 1929, as shown in Scheme 5:

Scheme 5

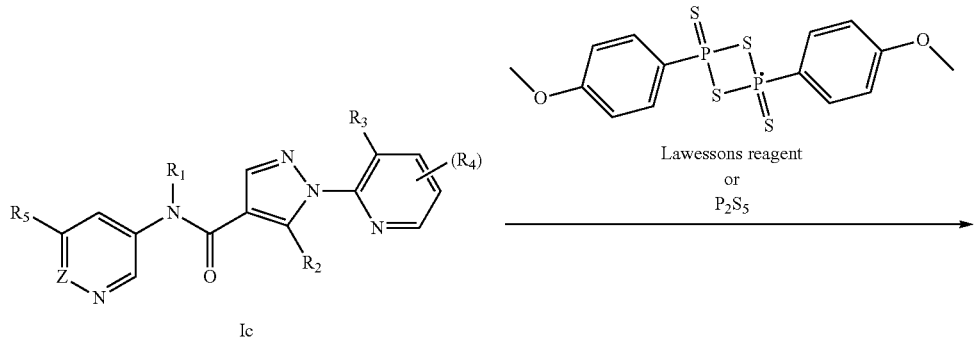

Lawessons reagent
or
$P_2S_5$

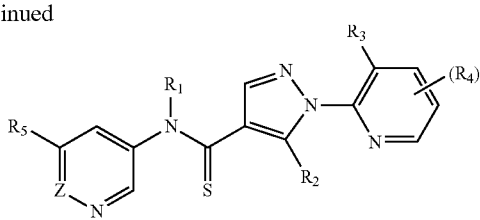

I where n is 0, X = S

Compounds of formula I, wherein X=oxygen and $R_2$ is methyl can be prepared from a compound of formula III by reacting with diketene to give a compound of formula VI, which reacts with dimethylformamide dimethyl acetal (DMF-DMA) to a compound of formula VII, which is condensed with a compound of formula VIII to a compound of formula Ib, as shown in scheme 6 and as described in e.g. J. M. Domagala, P. Peterson, *J. Heterocycl. Chem.* 1989, 26, 1147.

Scheme 6:

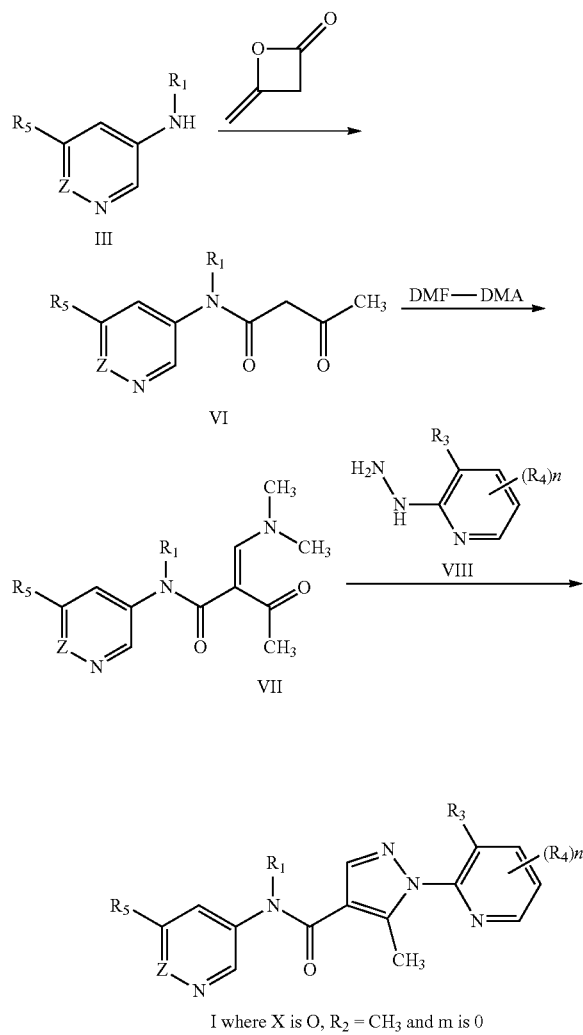

I where X is O, $R_2$ = $CH_3$ and m is 0

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties can be obtained in free form or in the form of salts.

The compounds of formula I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diastereomers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from *J. Med. Chem.* 1989, 32, 2561 or WO 2000/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds of formula I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i. e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50%.

The compounds of formula I can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fibre products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula I include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (*thrips*), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus*

(carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Bladtta orientalis* (cockroach), termites of the Mastotermitidae (for example *Mastotermes* spp.), the Kalotermitidae (for example *Neotermes* spp.), the Rhinotermitidae (for example *Coptotermes formosanus*, *Reticulitermes flavipes*, *R. speratu*, *R. virginicus*, *R. hesperus*, and *R. santonensis*) and the Termitidae (for example *Globitermes sulphureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

Further examples of the above mentioned pests are:

from the order Acarina, for example, *Acalitus* spp, *Aculus* spp, *Acaricalus* spp, *Aceria* spp, *Acarus siro*, *Amblyomma* spp., *Argas* spp., *Boophilus* spp., *Brevipalpus* spp., *Bryobia* spp, *Calipitrimerus* spp., *Chorioptes* spp., *Dermanyssus gallinae*, *Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polypha-gotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example, *Haematopinus* spp., *Linognathus* spp., *Pediculus* spp., *Pemphigus* spp. and *Phylloxera* spp.;

from the order Coleoptera, for example, *Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp, *Sphenophorus* spp, *Sternechus subsignatus*, *Tenebrio* spp., *Tribolium* spp. and *Trogoderma* spp.;

from the order Diptera, for example, *Aedes* spp., *Anopheles* spp, *Antherigona soccata*, *Bactrocea oleae*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;

from the order Hemiptera, for example, *Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp., *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp, *Murgantia histrionic*, *Neomegalotomus* spp, *Nesidiocoris tenuis*, *Nezara* spp., *Nysius simulans*, *Oebalus insularis*, *Piesma* spp., *Piezodorus* spp, *Rhodnius* spp., *Sahlbergella sing ularis*, *Scaptocoris castanea*, *Scotinophara* spp., *Thyanta* spp, *Triatoma* spp., *Vatiga illudens*; *Acyrthosium pisum*, *Adalges* spp, *Agalliana ensigera*, *Agonoscena targionii*, *Aleurodicus* spp, *Aleurocanthus* spp, *Aleurolobus barodensis*, *Aleurothrixus floccosus*, *Aleyrodes brassicae*, *Amarasca biguttula*, *Amritodus atkinsoni*, *Aonidiella* spp., *Aphididae*, *Aphis* spp., *Aspidiotus* spp., *Aulacorthum solani*, *Bactericera cockerelli*, *Bemisia* spp, *Brachycaudus* spp, *Brevicoryne brassicae*, *Cacopsylla* spp, *Cavariella aegopodii* Scop., *Ceroplaster* spp., *Chrysomphalus aonidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp, *Empoasca* spp., *Eriosoma larigerum*, *Erythroneura* spp., *Gascardia* spp., *Glycaspis brimblecombei*, *Hyadaphis pseudobrassicae*, *Hyalopterus* spp, *Hyperomyzus pallidus*, *Idioscopus clypealis*, *Jacobiasca lybica*, *Laodelphax* spp., *Lecanium corni*, *Lepidosaphes* spp., *Lopaphis erysimi*, *Lyogenys maidis*, *Macrosiphum* spp., *Mahanarva* spp, *Metcalfa pruinosa*, *Metopolophium dirhodum*, *Myndus crudus*, *Myzus* spp., *Neotoxoptera* sp, *Nephotettix* spp., *Nilaparvata* spp., *Nippolachnus piri* Mats, *Odonaspis ruthae*, *Oregma lanigera* Zehnter, *Parabemisia myricae*, *Paratrioza cockerelli*, *Parlatoria* spp., *Pemphigus* spp., *Peregrinus maidis*, *Perkinsiella* spp, *Phorodon humuli*, *Phylloxera* spp, *Planococcus* spp., *Pseudaulacaspis* spp., *Pseudococcus* spp., *Pseudatomoscelis seriatus*, *Psylla* spp., *Pulvinaria aethiopica*, *Quadraspidiotus* spp., *Quesada gigas*, *Recilia dorsalis*, *Rhopalosiphum* spp., *Saissetia* spp., *Scaphoideus* spp., *Schizaphis* spp., *Sitobion* spp., *Sogatella furcifera*, *Spissistulus festinus*, *Tarophagus Proserpina*, *Toxoptera* spp, *Trialeurodes* spp, *Tridiscus sporoboli*, *Trionymus* spp, *Trioza erytreae*, *Unaspis citri*, *Zygina flammigera*, *Zyginidia scutellaris*;

from the order Heteroptera, for example, *Cimex* spp., *Distantiella theobroma*, *Dysdercus* spp., *Euchistus* spp., *Eurygaster* spp., *Leptocorisa* spp., *Nezara* spp., *Piesma* spp., *Rhodnius* spp., *Sahlbergella singularis*, *Scotinophara* spp. and *Triatoma* spp.;

from the order Homoptera, for example, *Aleurothrixus floccosus*, *Aleyrodes brassicae*, *Aonidiella* spp., *Aphididae*, *Aphis* spp., *Aspidiotus* spp., *Bemisia tabaci*, *Ceroplaster* spp., *Chrysomphalus aonidium*, *Chrysomphalus dictyospermi*, *Coccus hesperidum*, *Empoasca* spp., *Eriosoma larigerum*, *Erythroneura* spp., *Gascardia* spp., *Laodelphax* spp., *Lecanium corni*, *Lepidosaphes* spp., *Macrosiphus* spp., *Myzus* spp., *Nephotettix* spp., *Nilaparvata* spp., *Parlatoria* spp., *Pemphigus* spp., *Planococcus* spp., *Pseudaulacaspis* spp., *Pseudococcus* spp., *Psylla* spp., *Pulvinaria aethiopica*, *Quadraspidiotus* spp., *Rhopalosiphum* spp., *Saissetia* spp., *Scaphoideus* spp., *Schizaphis* spp., *Sitobion* spp., *Trialeurodes vaporariorum*, *Trioza erytreae* and *Unaspis citri*;

from the order Hymenoptera, for example, *Acromyrmex, Arge* spp, *Atta* spp., *Cephus* spp., *Diprion* spp., *Diprionidae, Gilpinia polytoma, Hoplocampa* spp., *Lasius* spp., *Monomorium pharaonis, Neodiprion* spp., *Pogonomyrmex* spp, *Slenopsis invicta, Solenopsis* spp. and *Vespa* spp.;

from the order Isoptera, for example, *Coptotermes* spp, *Corniternes cumulans, Incisitermes* spp, *Macrotermes* spp, *Mastotermes* spp, *Microtermes* spp, *Reticulitermes* spp.; *Solenopsis geminate;* from the order Lepidoptera, for example, *Acleris* spp., *Adoxophyes* spp., *Aegeria* spp., *Agrotis* spp., *Alabama argillaceae, Amylois* spp., *Anticarsia gemmatalis, Archips* spp., *Argyresthia* spp, *Argyrotaenia* spp., *Autographa* spp., *Bucculatrix thurberiella, Busseola fusca, Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp, *Crocidolomia binotalis, Cryptophlebia leucotreta, Cydalima perspectalis, Cydia* spp., *Diaphania perspectalis, Diatraea* spp., *Diparopsis castanea, Earias* spp., *Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculiferia, Grapholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocollethis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp, *Operophtera* spp., *Orniodes indica, Ostrinia nubilalis, Pammene* spp., *Pandemis* spp., *Panolis flammea, Papaipema nebris, Pectinophora gossypiela, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusia nu, Richia albicosta, Scirpophaga* spp., *Sesamia* spp., *Sparganothis* spp., *Spodoptera* spp., *Sylepta derogate, Synanthedon* spp., *Thaumetopoea* spp., *Tortrix* spp., *Trichoplusia ni, Tuta absoluta,* and *Yponomeuta* spp.;

from the order Mallophaga, for example,

*Damalinea* spp. and *Trichodectes* spp.;

from the order Orthoptera, for example, *Blatta* spp., *Blattella* spp., *Gryllotalpa* spp., *Leucophaea maderae, Locusta* spp., *Neocurtilla hexadactyla, Periplaneta* spp., *Scapteriscus* spp, and *Schistocerca* spp.;

from the order Psocoptera, for example, *Liposcelis* spp.;

from the order Siphonaptera, for example, *Ceratophyllus* spp., *Ctenocephalides* spp. and *Xenopsylla cheopis;* from the order Thysanoptera, for example,

*Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp; and from the order Thysanura, for example, *Lepisma saccharina.*

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals.

The term "crops" is to be understood as including also crops that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady® and LibertyLink®.

The term "crops" is also to be understood as including also crop plants which have been so transformed by the use of recombinant DNA techniques that they are capable of synthesising one or more selectively acting toxins, such as are known, for example, from toxin-producing bacteria, especially those of the genus *Bacillus.*

Toxins that can be expressed by such transgenic plants include, for example, insecticidal proteins, for example insecticidal proteins from *Bacillus cereus* or *Bacillus popliae*; or insecticidal proteins from *Bacillus thuringiensis*, such as δ-endotoxins, e.g. CryIA(b), CryIA(c), CryIF, CryIF (a2), CryIIA(b), CryIIIA, CryIIIB(b1) or Cry9c, or vegetative insecticidal proteins (VIP), e.g. VIP1, VIP2, VIP3 or VIP3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as *Streptomycetes* toxins, plant lectins, such as pea lectins, barley lectins or snowdrop lectins; agglutinins; proteinase inhibitors, such as trypsine inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example CryIA(b), CryIA (c), CryIF, CryIF(a2), CryIIA(b), CryIIIA, CryIIIB(b1) or Cry9c, or vegetative insecticidal proteins (VIP), for example VIP1, VIP2, VIP3 or VIP3A, expressly also hybrid toxins, truncated toxins and modified toxins. Hybrid toxins are produced recombinantly by a new combination of different domains of those proteins (see, for example, WO 02/15701). Truncated toxins, for example a truncated CryIA(b), are known. In the case of modified toxins, one or more amino acids of the naturally occurring toxin are replaced. In such amino acid replacements, preferably non-naturally present protease recognition sequences are inserted into the toxin, such as, for example, in the case of CryIIIA055, a cathepsin-D-recognition sequence is inserted into a CryIIIA toxin (see WO 03/018810). Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); NatureGard® Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated CryIA(b) toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a CryIIIB(b1) toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003.

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Crops may also be modified for enhanced resistance to fungal (for example *Fusarium, Anthracnose,* or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerance to abiotic stress include those that have enhanced tolerance to drought, high salt, high temperature, chill, frost, or light radiation, for example through expression of NF-YB or other proteins known in the art.

Crops that exhibit enhanced yield or quality include those with improved flowering or fruit ripening properties (such as delayed ripening); modified oil, starch, amino acid, fatty acid, vitamin, phenolic or other content (such as Vistive™ soybean variety); enhanced nutrient utilisation (such as improved nitrogen assimilation); and enhanced quality plant product (such as higher quality cotton fibre).

Further areas of use of the compounds and compositions according to the invention are the protection of stored goods and storerooms and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO2006/128870, EP 1724392, WO2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B:

TABLE A

Examples of exotic woodborers of economic importance.

| Family | Species | Host or Crop Infested |
|---|---|---|
| Buprestidae | Agrilus planipennis | Ash |
| Cerambycidae | Anoplura glabripennis | Hardwoods |
| Scolytidae | Xylosandrus crassiusculus | Hardwoods |
|  | X. mutilatus | Hardwoods |
|  | Tomicus piniperda | Conifers |

TABLE B

Examples of native woodborers of economic importance.

| Family | Species | Host or Crop Infested |
|---|---|---|
| Buprestidae | Agrilus anxius | Birch |
|  | Agrilus politus | Willow, Maple |
|  | Agrilus sayi | Bayberry, Sweetfern |
|  | Agrilus vittaticolllis | Apple, Pear, Cranberry, Serviceberry, Hawthorn |
|  | Chrysobothris femorata | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
|  | Texania campestris | Basswood, Beech, Maple, Oak, Sycamore, Willow, Yellow-poplar |
| Cerambycidae | Goes pulverulentus | Beech, Elm, Nuttall, Willow, Black oak, Cherrybark oak, Water oak, Sycamore |
|  | Goes tigrinus | Oak |
|  | Neoclytus acuminatus | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
|  | Neoptychodes trilineatus | Fig, Alder, Mulberry, Willow, Netleaf hackberry |
|  | Oberea ocellata | Sumac, Apple, Peach, Plum, Pear, Currant, Blackberry |
|  | Oberea tripunctata | Dogwood, Viburnum, Elm, Sourwood, Blueberry, Rhododendron, Azalea, Laurel, Poplar, Willow, Mulberry |
|  | Oncideres cingulata | Hickory, Pecan, Persimmon, Elm, Sourwood, Basswood, Honeylocust, Dogwood, Eucalyptus, Oak, Hackberry, Maple, Fruit trees |
|  | Saperda calcarata | Poplar |
|  | Strophiona nitens | Chestnut, Oak, Hickory, Walnut, Beech, Maple |
| Scolytidae | Corthylus columbianus | Maple, Oak, Yellow-poplar, Beech, Boxelder, Sycamore, Birch, Basswood, Chestnut, Elm |
|  | Dendroctonus frontalis | Pine |
|  | Dryocoetes betulae | Birch, Sweetgum, Wild cherry, Beech, Pear |
|  | Monarthrum fasciatum | Oak, Maple, Birch, Chestnut, Sweetgum, Blackgum, Poplar, Hickory, Mimosa, Apple, Peach, Pine |

TABLE B-continued

Examples of native woodborers of economic importance.

| Family | Species | Host or Crop Infested |
|---|---|---|
| | Phloeotribus liminaris | Peach, Cherry, Plum, Black cherry, Elm, Mulberry, Mountain-ash |
| | Pseudopityophthorus pruinosus | Oak, American beech, Black cherry, Chickasaw plum, Chestnut, Maple, Hickory, Hornbeam, Hophornbeam |
| Sesiidae | Paranthrene simulans | Oak, American chestnut |
| | Sannina uroceriformis | Persimmon |
| | Synanthedon exitiosa | Peach, Plum, Nectarine, Cherry, Apricot, Almond, Black cherry |
| | Synanthedon pictipes | Peach, Plum, Cherry, Beach, Black Cherry |
| | Synanthedon rubrofascia | Tupelo |
| | Synanthedon scitula | Dogwood, Pecan, Hickory, Oak, Chestnut, Beech, Birch, Black cherry, Elm, Mountain-ash, Viburnum, Willow, Apple, Loquat, Ninebark, Bayberry |
| | Vitacea polistiformis | Grape |

In the hygiene sector, the compounds and compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp., Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis*, *Periplaneta americana*, *Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compounds and compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus*, *Chlorophorus pilosis*, *Anobium punctatum*, *Xestobium rufovillosum*, *Ptilinuspecticornis*, *Dendrobium pertinex*, *Ernobius mollis*, *Priobium carpini*, *Lyctus brunneus*, *Lyctus africanus*, *Lyctus planicollis*, *Lyctus linearis*, *Lyctus pubescens*, *Trogoxylon aequale*, *Minthesrugicollis*, *Xyleborus* spec., *Tryptodendron* spec., *Apate monachus*, *Bostrychus capucins*, *Heterobostrychus brunneus*, *Sinoxylon* spec. and *Dinoderus minutus*, and also hymenopterans such as *Sirex juvencus*, *Urocerus gigas*, *Urocerus gigas taignus* and *Urocerus augur*, and termites such as *Kalotermes flavicollis*, *Cryptotermes brevis*, *Heterotermes indicola*, *Reticulitermes flavipes*, *Reticulitermes santonensis*, *Reticulitermes lucifugus*, *Mastotermes darwiniensis*, *Zootermopsis nevadensis* and *Coptotermes formosanus*, and bristletails such as *Lepisma saccharina*.

The present invention therefore provides an insecticidal, acaricidal, nematicidal or molluscicidal composition, preferably an insecticidal or acaricidal composition comprising an insecticidally, acaricidally, nematicidally or molluscicidally effective amount of a compound of formula I and a suitable carrier or diluent therefor.

In a further aspect the invention provides a method of combating and controlling pests which comprises applying an insecticidally, acaricidally, nematicidally or molluscicidally effective amount, preferably an insecticidally and acaricidally effective amount of a compound of formula I or a composition comprising a compound of formula I, to a pest, a locus of pest, or to a plant susceptible to attack by a pest, with the exception of a method for treatment of the human or animal body by surgery or therapy and diagnostic methods practised on the human or animal body.

The compounds of formula I are preferably used against insects or acarines.

The term "plant" as used herein includes seedlings, bushes and trees.

The invention also relates to a pesticidal composition, which, in addition to comprising the compound of formula I, comprises formulation adjuvants.

The invention therefore also relates to pesticidal compositions such as emulsifiable concentrates, suspension concentrates, directly sprayable or dilutable solutions, spreadable pastes, dilute emulsions, soluble powders, dispersible powders, wettable powders, dusts, granules or encapsulations in polymeric substances, which comprise—at least—one of the active ingredients according to the invention and which are to be selected to suit the intended aims and the prevailing circumstances.

In these compositions, the active ingredient is employed in pure form, a solid active ingredient for example in a specific particle size, or, preferably, together with—at least—one of the auxiliaries conventionally used in the art of formulation, such as extenders, for example solvents or solid carriers, or such as surface-active compounds (surfactants).

Examples of suitable solvents are: unhydrogenated or partially hydrogenated aromatic hydrocarbons, preferably the fractions C8 to C12 of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers. Suitable particulate adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopolypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylphenoxypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quaternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethylammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and a fatty acid radical of approximately 8 to approximately 22 C atoms. Examples of alkylarylsulfonates are the sodium, calcium or triethanolammonium salts of decylbenzenesulfonic acid, of dibutylnaphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids. Further suitable phosphates are tris-esters of phosphoric acid with aliphatic or aromatic alcohols and/or bis-esters of alkyl phosphonic acids with aliphatic or aromatic alcohols, which are a high performance oil-type adjuvant. These tris-esters have been described, for example, in WO 01/47356, WO 00/56146, EP-A-0579052 or EP-A-1018299 or are commercially available under their chemical name. Preferred tris-esters of phosphoric acid for use in the new compositions are tris-(2-ethylhexyl) phosphate, tris-n-octyl phosphate and tris-butoxyethyl phosphate, where tris-(2-ethylhexyl) phosphate is most preferred. Suitable bis-ester of alkyl phosphonic acids are bis-(2-ethylhexyl)-(2-ethylhexyl)-phosphonate, bis-(2-ethylhexyl)-(n-octyl)-phosphonate, dibutyl-butyl phosphonate and bis(2-ethylhexyl)-tripropylene-phosphonate, where bis-(2-ethylhexyl)-(n-octyl)-phosphonate is particularly preferred.

The compositions according to the invention can preferably additionally include an additive comprising an oil of vegetable or animal origin, a mineral oil, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil such as ADIGOR® and MERO®, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000. Also, alkoxylated fatty acids can be used as additives in the inventive compositions as well as polymethylsiloxane based additives, which have been described in WO 2008/037373.

The application and action of the oil additives can be further improved by combining them with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyloxide-modified heptamethyltrisiloxanes, which are commercially available e.g. as Silwet L-77®, and also perfluorinated surfactants. The concentration of surface-active substances in relation to the total additive is generally from 1 to 30% by weight. Examples of oil additives that consist of mixtures of oils or mineral oils or derivatives thereof with surfactants are Edenor ME SU®, Turbocharge® (Syngenta AG, CH) and Actipron® (BP Oil UK Limited, GB).

The said surface-active substances may also be used in the formulations alone, that is to say without oil additives.

Furthermore, the addition of an organic solvent to the oil additive/surfactant mixture can contribute to a further enhancement of action. Suitable solvents are, for example, Solvesso® (ESSO) and Aromatic Solvent® (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada.)

In addition to the oil additives listed above, in order to enhance the activity of the compositions according to the invention it is also possible for formulations of alkylpyrrolidones, (e.g. Agrimax®) to be added to the spray mixture. Formulations of synthetic latices, such as, for example, polyacrylamide, polyvinyl compounds or poly-1-p-menthene (e.g. Bond®, Courier® or Emerald®) can also be used. Solutions that contain propionic acid, for example Eurogkem Pen-e-trate®, can also be mixed into the spray mixture as activity-enhancing agents.

The term "active ingredient" refers to one of the compounds of formula I, especially the compounds of formula I specifically disclosed in the tables. It also refers to mixtures of the compound of formula I, in particular a compound selected from said Table 1, with other insecticides, fungicides, herbicides, safeners, adjuvants and the like, which mixtures are specifically disclosed below.

The compositions can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers; fertilizers, in particular nitrogen containing fertilizers such as ammonium nitrates and urea as described in WO 2008/017388, which can enhance the efficacy of the inventive compounds; or other active ingredients for achieving specific effects, for example ammonium or phosphonium salts, in particular halides, (hydrogen)sulphates, nitrates, (hydrogen)carbonates, citrates, tartrates, formiates and acetates, as described in WO 2007/068427 and WO 2007/068428, which also can enhance the efficacy of the inventive compounds and which can be used in combination with penetration enhancers such as alkoxalated fatty acids; bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries).

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compositions according to the invention are also suitable for the protection of plant propagation material, for example seeds, such as fruit, tubers or kernels, or nursery plants, against pests of the abovementioned type. The propagation material can be treated with the compositions prior to planting, for example seed can be treated prior to sowing. Alternatively, the compositions can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material comprising a compound of formula I as defined above are further subjects of the invention.

Further methods of application of the compositions according to the invention comprise drip application onto the soil, dipping of parts of plants such as roots bulbs or tubers, drenching the soil, as well as soil injection. These methods are known in the art.

In order to apply a compound of formula I as an insecticide, acaricide, nematicide or molluscicide to a pest, a locus of pest, or to a plant susceptible to attack by a pest, a compound of formula I is usually formulated into a composition which includes, in addition to the compound of formula I, a suitable inert diluent or carrier and, optionally, a formulation adjuvant in form of a surface active agent (SFA) as described herein or, for example, in EP-B-1062217. SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting).

As a rule, the compositions comprise 0.1 to 99%, especially 0.1 to 95%, of active ingredient of the formula I and 1 to 99.9%, especially 5 to 99.9%, of at least one solid or liquid adjuvant, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

When used in a seed dressing, a compound of formula I is used at a rate of 0.0001 g to 10 g (for example 0.001 g or 0.05 g), preferably 0.005 g to 10 g, more preferably 0.005 g to 4 g, per kilogram of seed.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), microemulsions (ME), suspension concentrates (SC), oil-based suspension concentrate (OD), aerosols, fogging/smoke formulations, capsule suspensions (CS) and seed treatment formulations. The formulation type chosen in any instance will depend upon the particular purpose en-visaged and the physical, chemical and biological properties of the compound of formula I.

Dustable powders (DP) may be prepared by mixing a compound of formula I with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula I with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula I with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula I and one or more powdered solid diluents or carriers, or from pre-formed blank granules by absorbing a compound of formula I (or a solution thereof, in a suitable agent) in a porous granular material (such as pumice, attapulgite clays, fullers earth, kieselguhr, diatomaceous earths or ground corn cobs) or by adsorbing a compound of formula I (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent). Dispersible Concentrates (DC) may be prepared by dissolving a compound of formula I in water or an organic solvent, such as a ketone, alcohol or glycol ether. These solutions may contain a surface active agent (for example to improve water dilution or prevent crystallisation in a spray tank). Emulsifiable concentrates (EC) or oil-in-water emulsions (EW) may be prepared by dissolving a compound of formula I in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula I either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water. Microemulsions (ME) may be prepared by mixing water with a blend of one or more solvents with one or more SFAs, to produce spontaneously a thermodynamically stable isotropic liquid formulation. A compound of formula I is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula I. SCs may be prepared by ball or bead milling the solid compound of formula I in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula I may be dry milled and added to water, containing agents hereinbefore described, to produce the desired end product.

Oil-based suspension concentrate (OD) may be prepared similarly by suspending finely divided insoluble solid particles of a compound of formula I in an organic fluid (for example at least one mineral oil or vegetable oil). ODs may further comprise at least one penetration promoter (for example an alcohol ethoxylate or a related compound), at least one non-ionic surfactants and/or at least one anionic surfactant, and optionally at least one additive from the group of emulsifiers, foam-inhibiting agents, preservatives, anti-oxidants, dyestuffs, and/or inert filler materials. An OD is intended and suitable for dilution with water before use to produce a spray solution with sufficient stability to allow spray application through appropriate equipment.

Aerosol formulations comprise a compound of formula I and a suitable propellant (for example n-butane). A compound of formula I may also be dissolved or dispersed in a suitable medium (for example water or a water miscible liquid, such as n-propanol) to provide compositions for use in non-pressurised, hand-actuated spray pumps.

A compound of formula I may be mixed in the dry state with a pyrotechnic mixture to form a composition suitable for generating, in an enclosed space, a smoke containing said compound. Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula I and, optionally, a carrier or diluent therefor. The polymeric shell may be produced by either an interfacial polycondensation reaction or by a coacervation procedure. The compositions may provide for controlled release of the compound of formula I and they may be used for seed treatment. A compound of formula I may also be formulated in a biodegradable polymeric matrix to provide a slow, controlled release of the compound.

A compound of formula I may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC, OD and DC compositions described above. Compositions for treating seed may include an agent for assisting the adhesion of the composition to the seed (for example a mineral oil or a film-forming barrier). A composition of the present invention may include one or more additives to improve the biological performance of the composition (for example by improving wetting, retention or distribution on surfaces; resistance to rain on treated surfaces; or uptake or mobility of a compound of formula I). Such additives include surface active agents (SFAs), spray additives based on oils, for example certain mineral oils, vegetable oils or natural plant oils (such as soy bean and rape seed oil), and blends of these with other bio-enhancing adjuvants (ingredients which may aid or modify the action of a compound of formula I). Increasing the effect of a compound of formula I may for example be achieved by adding ammonium and/or phosphonium salts, and/or optionally at least one penetration promotor such as fatty alcohol alkoxylates (for example rape oil methyl ester) or vegetable oil esters. Wetting agents, dispersing agents and emulsifying agents may be surface active agents (SFAs) of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula I may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula I may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ODs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula I (for example 0.0001 to 10%, by weight) depending upon the purpose for which they are to be used.

A compound of formula I may be used in mixtures with fertilisers (for example nitrogen-, potassium- or phosphorus-containing fertilisers, and more particularly ammonium nitrate and/or urea fertilizers). Suitable formulation types include granules of fertiliser. The mixtures suitably contain up to 25% by weight of the compound of formula I.

Preferred compositions are composed in particular as follows (%=percent by weight):
Emulsifiable Concentrates:
active ingredient: 1 to 95%, preferably 5 to 20%
surfactant: 1 to 30%, preferably 10 to 20%
solvent: 5 to 98%, preferably 70 to 85%
Dusts:
active ingredient: 0.1 to 10%, preferably 0.1 to 1%
solid carrier: 99.9 to 90%, preferably 99.9 to 99%
Suspension Concentrates:
active ingredient: 5 to 75%, preferably 10 to 50%
water: 94 to 24%, preferably 88 to 30%
surfactant: 1 to 40%, preferably 2 to 30%
Wettable Powders:
active ingredient: 0.5 to 90%, preferably 1 to 80%
surfactant: 0.5 to 20%, preferably 1 to 15%
solid carrier: 5 to 99%, preferably 15 to 98%
Granulates:
active ingredient: 0.5 to 30%, preferably 3 to 15%
solid carrier: 99.5 to 70%, preferably 97 to 85%

PREPARATORY EXAMPLES

The invention is illustrated by the following preparation examples.

Example 1: 1-(3-methylpyridin-2-yl)-5-methyl-1H-pyrazole-4-carboxylic acid methyl-pyridin-3-yl-amide. (Compound No. 1.001)

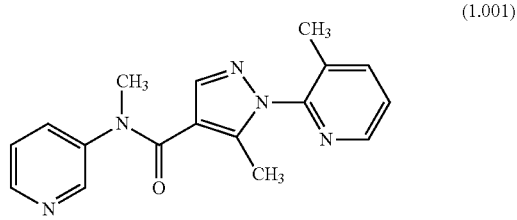 [SMILES: Cc1cccnc1-n1ncc(C(=O)N(C)c2cccnc2)c1C]

(1.001)

To a solution of 1-(3-methylpyridin-2-yl)-5-methyl-1H-pyrazole-4-carboxylic acid (1.2 g, 5.5 mmol) in dichloromethane (44 ml) was added oxalyl chloride (2.1 g, 17.0 mmol) followed by two drops of dimethylformamide. The reaction was stirred for two hours at ambient temperature after which time the solvent was evaporated. The crude acid chloride was dissolved in tetrahydrofuran (20 ml) and added to a solution of 3-methylaminopyridine (0.47 g, 4.2 mmol) and triethylamine (0.86 g, 8.5 mmol) in tetrahydrofuran (10 ml) at ambient temperature. The reaction was stirred at ambient temperature for 6 hours after which time saturated ammonium chloride was added and the mixture extracted three times with ethyl acetate. The combined organic phases were dried and evaporated and the crude product was purified by flash column chromatography (silica using dichloromethane/methanol 9:1) to give 1.3 g of the title compound as an oil. 1H NMR (CDCl$_3$): 2.1 (s, 3H), 2.4 (s, 3H), 3.5 (s, 3H), 6.7 (s, 1H), 7.3 (m, 2H), 7.55 (m, 1H), 7.7 (m, 1H), 8.4 (m, 1H), 8.55 (m, 2H).

The starting materials can be prepared as follows:

1-(3-methylpyridin-2-yl)-5-methyl-1H-pyrazole-4-carboxylic acid

To a solution of 1-(3-methylpyridin-2-yl)-5-methyl-1H-pyrazole-4-carboxylic acid methyl ester (18.50 g, 80.0 mmol) in tetrahydrofuran (160 ml) was added sodium hydroxide (4.80 g, 120.0 mmol) in a mixture of methanol (80 ml) and water (80 ml) and the reaction was stirred at ambient temperature for 2 hours. The reaction was then acidified using 2N HCl to pH=1 and the crude product extracted three times with ethyl acetate. The combined organic phases were dried and the solvent evaporated to give a crude product which was stirred with dichloromethane, filtered and dried to give 14.25 g of the title compound as a solid, with melting point 157-158° C. $^1$H NMR (CDCl3): 2.2 (s, 3H), 2.5 (s, 3H), 7.4 (m, 1H), 7.8 (m, 1H), 8.1 (m, 1H), 8.5 (M, 1H).

1-(3-methylpyridin-2-yl)-5-methyl-1H-pyrazole-4-carboxylic acid methyl ester

To a solution of ethyl 2-((dimethylamino)methylene)-3-oxobutanoate (18.5 g, 80 mmol) in ethanol (250 ml) was added (3-methylpyridin-2-yl)-hydrazine (10.0 g, 81 mmol) and the reaction was stirred at reflux for 4 hours. After cooling to ambient temperature, the solvent was evaporated and the crude treated with water and extracted three times with ethyl acetate. The combined organic phases were dried and evaporated to give the title compound as a solid, with melting point 56-57° C. 1H NMR (CDCl$_3$): 2.2 (s, 3H), 2.5 (s, 3H), 4.9 (s, 3H), 7.35 (m, 1H), 7.75 (m, 1H), 8.05 (s, 1H), 8.45 (M, 1H).

Example 2: 1-(3-methylpyridin-2-yl)-5-methyl-1H-pyrazole-4-carboxylic acid methyl-pyridin-N-oxide-3-yl-amide. (Compound No. 1.079)

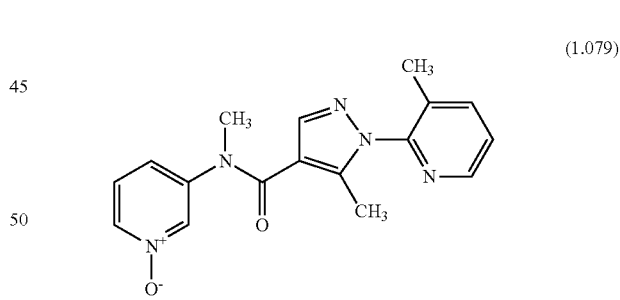

(1.079)

To a solution of 1-(3-methylpyridin-2-yl)-5-methyl-1H-pyrazole-4-carboxylic acid methyl-pyridin-3-yl-amide (0.20 g, 0.65 mmol) in chloroform (1.5 ml) was added at 0° C. meta chloroperbenzoic acid (0.32 g, 1.8 mmol) and the reaction was stirred at ambient temperature for 3 hours. The reaction mixture was then made basic (pH=14) and the crude product extracted into dichloromethane. The organic phase was dried and the solvent evaporated; the crude product was purified by flash column chromatography (silica using dichloromethane/methanol 9:1) to give 0.04 g of the title compound as a gum. $^1$H NMR (CDCl3): 2.2 (s, 3H), 2.31 (s, 3H), 3.49 (s, 3H), 7.13 (dd, 1H), 7.2-7.31 (m, 4H), 8.1 (d, 1H), 8.20 (d, 1H), 8.24 (m, 1H).

Example 3: 1-(3-methylpyridin-2-yl)-5-methyl-1H-pyrazole-4-carboxylic acid methyl-pyridin-3-yl-amide. (Compound No. 1.001)

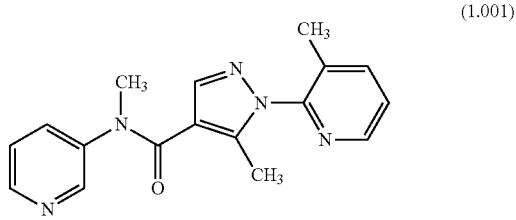 [SMILES: Cc1cccnc1-n1ncc(C(=O)N(C)c2cccnc2)c1C]

(1.001)

To a solution of 2-(1-dimethylamino-methylidene)-N-methyl-3-oxo-N-pyridin-3-yl-butyramide (6.18 g, 25.0 mmol) in ethanol (100 ml) was added (3-methylpyridin-2-yl)-hydrazine (3.08 g, 25.0 mmol) and the reaction was stirred at reflux for 48 hours. After cooling to ambient temperature, the solvent was evaporated and the crude treated with water and extracted three times with ethyl acetate. The combined organic phases were dried and purified by flash chromatography (silica using dichloromethane/methanol 9:1) to give 5.2 g of the title compound as a gum identical to that prepared as described in Example 1 above.

The starting materials can be prepared as follows:

2-(1-dimethylamino-methylidene)-N-methyl-3-oxo-N-pyridin-3-yl-butyramide

To a solution of N-methyl-3-oxo-N-pyridin-3-yl-butyramide (0.48 g, 2.5 mmol) in tetrahydrofuran (2.5 ml) was added dimethyl acetal dimethyl formamide (0.63 g, 5.0 mmol) together with acetic acid (0.3 g, 5.0 mmol) and the reaction was stirred at ambient temperature for 3 hours. The solvent was then evaporated and the crude material purified by flash chromatography (silica using dichloromethane/methanol 9:1) to give 0.43 g of the title compound as a red gum. $^1$H NMR (CDCl3): 1.9 (s, 3H), 3.1 (br. s, 6H), 3.4 (s, 3H), 7.0 (br, 1H), 7.25 (br, 1H), 7.55 (br, 1H), 8.35 (br, 1H), 8.45 (br, 1H).

N-Methyl-3-oxo-N-pyridin-3-yl-butyramide

To a solution of N-methylpyridin-3-amine (5.4 g, 50 mmol) in tetrahydrofuran (100 ml) was added dropwise diketene (5.04 g, 60 mmol) in tetrahydrofuran (50 ml). The mixture was then heated to reflux for 2 hours, and then a further amount of diketene (5.04 g, 60 mmol) was added and the reaction heated to reflux overnight. The solvent was then evaporated and the crude material purified by flash chromatography (silica using heptane/ethyl acetate 5:1) to give 2.76 g of the title compound as an oil, which exists as a mixture of keto-enol isomers as shown by $^1$H NMR.

Example 4: 1-(5-bromo-3-methyl-2-pyridyl)-N,5-dimethyl-N-(3-pyridyl)pyrazole-4-carboxamide (Compound No. 1.003)

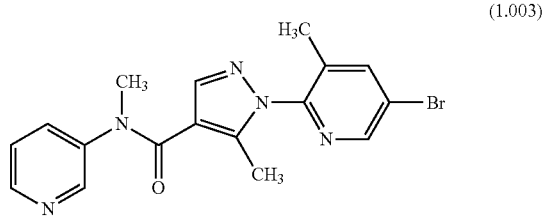 [SMILES: Cc1cc(Br)cnc1-n1ncc(C(=O)N(C)c2cccnc2)c1C]

(1.003)

(5-bromo-3-methyl-2-pyridyl)hydrazine (16 g, 79.2 mmol, prepared as described in WO 2012050159) and 2-(1-dimethylamino-methylidene)-N-methyl-3-oxo-N-pyridin-3-yl-butyramide (20 g, 80.87 mmol) were dissolved in 200 ml of ethanol and stirred for 12 hours at 90° C. The mixture was concentrated in vacuo, and purified by flash chromatography eluting with a gradient of ethyl acetate 100% toethyl acetate:methanol 19:1. This yielded the title compound (17.8 g, 57%) as a honey.
$^1$H NMR (CDCl$_3$): 2.10 (s, 3H), 2.41 (s, 3H), 3.49 (s, 3H), 6.71 (s, 1H), 7.32 (m, 1H), 7.84 (m, 1H), 8.45 (br, 1H), 8.53 (m, 2H).

Example 5: 1-(5-cyano-3-methyl-2-pyridyl)-N,5-dimethyl-N-(3-pyridyl)pyrazole-4-carboxamide (Compound No. 1.004)

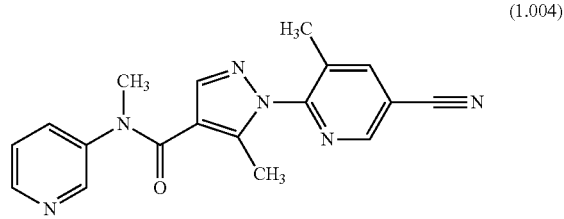 [SMILES: Cc1cc(C#N)cnc1-n1ncc(C(=O)N(C)c2cccnc2)c1C]

(1.004)

A solution of 1-(5-bromo-3-methyl-2-pyridyl)-N,5-dimethyl-N-(3-pyridyl)pyrazole-4-carboxamide (489 mg, 1.23 mmol, 1.0 eq.) in pyridine (5 ml) was treated with copper cyanide (168 mg, 1.88 mmol, 1.5 eq.), loaded to a microwave tube and irradiated for 3 hours at 170° C. The mixture was diluted with 20 ml of ethyl acetate and filtrated over a pad of Hyflo. The filtrate was washed successively with 10 ml aqueous sat. NH$_4$Cl sol., 10 ml water and 10 ml brine. The water phase was back extracted twice with ethyl acetate, and the combined organic phases dried over MgSO$_4$, filtrated and evaporated in vacuo. The crude reaction mixture was purified over silica gel cartridge (Rf200) eluting with ethyl acetate to give the title product (408 mg) as white crystals. LCMS (Method ZDQ13), 0.67 min, 333 (MH+).

Example 6: 1-(3-ethyl-2-pyridyl)-N,5-dimethyl-N-(3-pyridyl)pyrazole-4-carboxamide (Compound No. 1.025)

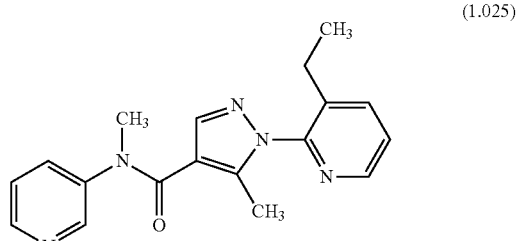

(1.025)

A solution of 1-(3-vinyl-2-pyridyl)-N,5-dimethyl-N-(3-pyridyl)pyrazole-4-carboxamide (102 mg, 0.319 mmol) in ethanol (6.5 ml) was hydrogenated using a H-Cube apparatus, whereby the catalyst was 10% Palladium on Charcoal, at a pressure of 20 bar, and a temperature of 25° C. After removal of solvent, the crude reaction mixture was purified over silica gel cartridge (Rf200) eluting with acetonitrile-water mixtures to give the title product (55 mg) as an oil. LCMS: 0.82 min, 322 (MH+).

The starting material can be prepared as follows:

1-(3-vinyl-2-pyridyl)-N,5-dimethyl-N-(3-pyridyl) pyrazole-4-carboxamide

To a solution of 1-(3-bromo-2-pyridyl)-N,5-dimethyl-N-(3-pyridyl)pyrazole-4-carboxamide (1.49 g, 4.0 mmol) in toluene (30 ml) was added triphenylphosphine (0.21 g, 0.8 mmol), tetrakistriphenylphosphinepalladium (0.37 g, 0.32 mmol) and tri-n-butylvinyl tin (1.59 g, 4.8 mmol) and the reaction was heated to 110° C. and stirred for two hours. After cooling to room temperature, the reaction was quenched with water and extracted twice with ethyl acetate. After removal of solvent, the crude reaction mixture was purified over silica gel cartridge (Rf200) eluting with ethyl acetate to give the title product (1007 mg) as white crystals with melting point 113-115° C. LCMS: 0.82 min, 320 (MH+).

Example 7: Preparation of 1-(6-chloro-3-methyl-2-pyridyl)-N,5-dimethyl-N-pyridazin-4-yl-pyrazole-4-carboxamide. (Compound No. 1.230)

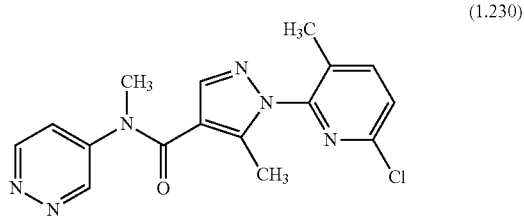 [SMILES: Cc1ccc(Cl)nc1-n1ncc(C(=O)N(C)c2ccnnc2)c1C]

(1.230)

To a solution of N-methylpyridazin-4-amine (83 mg, 0.76 mmol), triethylamine (0.42 ml, 3.04 mmol) and a catalytic amount of DMAP in 15 ml THF was added a solution in $CH_2Cl_2$ (5 ml) of 1-(6-chloro-3-methyl-2-pyridyl)-5-methyl-pyrazole-4-carbonyl chloride (0.21 g, 0.76 mmol), prepared from the corresponding acid (oxalyl chloride 5 eq., $CH_2Cl_2$, cat. DMF, 40° C., 5 h). The mixture was stirred at rt overnight. After evaporation of the solvents, the residue was taken up in ethyl acetate and washed with a solution of sodium bicarbonate. After drying ($MgSO_4$) and evaporating the organic phase, the residue was purified by flash chromatography to give the title compound as white crystals. Mp: 190-4° C., LCMS: 0.69 min, 343-5 (MH+).

The starting material can be prepared as follows:

1-(6-chloro-3-methyl-2-pyridyl)-5-methyl-pyrazole-4-carboxylic acid

A solution of methyl 1-(6-chloro-3-methyl-2-pyridyl)-5-methyl-pyrazole-4-carboxylate (270 mg, 1 mmol) and 240 mg NaOH (6 mmol) in methanol (4 ml) was stirred at rt overnight. The solvent was evaporated and the residue was taken up in a 2N HCl solution. The crystals formed were filtered and dried. Mp: 188-190° C.

methyl 1-(6-chloro-3-methyl-2-pyridyl)-5-methyl-pyrazole-4-carboxylate and methyl 1-(4-chloro-3-methyl-2-pyridyl)-5-methyl-pyrazole-4-carboxylate Methyl 5-methyl-1-(3-methyl-1-oxido-pyridin-1-ium-2-yl)pyrazole-4-carboxylate (3 g, 12.1 mmol) was suspended in 15 ml toluene. Phosphoroxychloride (5 ml, 82 mmol) was added and the mixture was heated at 60° C. overnight. After evaporation of the volatiles, the residue was suspended in water, and neutralized with a solution of sodium bicarbonate and basified with a 2N NaOH solution. The solution was extracted with ethyl acetate. The organic phase was dried over $MgSO_4$ and evaporated and the residue was submitted to flash chromatography (toluene 9, ethyl acetate 1). Methyl 1-(6-chloro-3-methyl-2-pyridyl)-5-methyl-pyrazole-4-carboxylate (1.0 g, mp: 126-7° C.) first eluted, followed by methyl 1-(4-chloro-3-methyl-2-pyridyl)-5-methyl-pyrazole-4-carboxylate (1.4 g, mp: 113-4° C.).

Methyl 5-methyl-1-(3-methyl-1-oxido-pyridin-1-ium-2-yl)pyrazole-4-carboxylate

To a solution of methyl 5-methyl-1-(3-methyl-2-pyridyl) pyrazole-4-carboxylate (7 g, 30.3 mmol) in 80 ml $CH_2Cl_2$ was added methyl trioxorhenium (VII) (100 mg, 0.31 mmol) and a 35% solution of hydrogen peroxide (5.21 ml, 60.5 mmol). After 5 h stirring at rt, a new portion of methyl trioxorhenium (VII) (100 mg, 0.31 mmol) and a 35% solution of hydrogen peroxide (2.0 ml, 23.2 mmol) were added. The solution was stirred three days at rt. After dilution with 250 ml $CH_2Cl_2$ and 100 ml water, the organic phase was treated with a solution of sodium thiosulfate to destroy the excess of peroxide. After drying the organic phase ($MgSO_4$) and evaporating, the residue was crystallized from ether/petrol ether to give the desired compound as a white solid. Mp: 92-3° C.

The compounds according to the following Tables 1 below can be prepared according to the methods described above. The examples which follow are intended to illustrate the invention and show preferred compounds of formula I.

Throughout this description, temperatures are given in degrees Celsius and "m.p." means melting point. LC/MS means Liquid Chromatography Mass Spectroscopy and the description of the apparatus and the method is:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 0% B, 100% A; 1.2-1.5 min 100% B; Flow (ml/min) 0.85

TABLE 1

This table discloses compounds No. 1.001 to 1.267

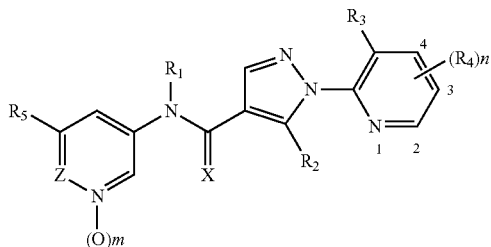

| Comp. No. | X | Z | m | R₁ | R₂ | R₃ | R₄ | R₅ | LCMS |
|---|---|---|---|---|---|---|---|---|---|
| 1.001 | O | C—H | 0 | CH₃ | CH₃ | CH₃ | H | H | 308 (M + 1) 0.59 min |
| 1.002 | O | C—H | 0 | CH₃ | CH₃ | CH₃ | 3-Cl | H | 342/4 (M + 1) 0.73 min |
| 1.003 | O | C—H | 0 | CH₃ | CH₃ | CH₃ | 3-Br | H | 386/8 (M + 1) 0.76 min |
| 1.004 | O | C—H | 0 | CH₃ | CH₃ | CH₃ | 3-CN | H | 333 (M + 1) 0.67 min |
| 1.005 | O | C—H | 0 | CH₃ | CH₃ | CH₃ | 3-CF₃ | H | |
| 1.006 | O | C—H | 0 | CH₃ | CH₃ | CH₃ | 3-CH₃ | H | |
| 1.007 | O | C—H | 0 | CH₂CH₃ | CH₃ | CH₃ | H | H | 322 (M + 1) 0.65 min |
| 1.008 | O | C—H | 0 | CH₂CH₃ | CH₃ | CH₃ | 3-Cl | H | |
| 1.009 | O | C—H | 0 | CH₂CH₃ | CH₃ | CH₃ | 3-Br | H | |
| 1.010 | O | C—H | 0 | CH₂CH₃ | CH₃ | CH₃ | 3-CN | H | |
| 1.011 | O | C—H | 0 | CH₂CH₃ | CH₃ | CH₃ | 3-CF₃ | H | |
| 1.012 | O | C—H | 0 | CH₂CH₃ | CH₃ | CH₃ | 3-CH₃ | H | |
| 1.013 | O | C—H | 0 | HC≡CCH₂ | CH₃ | CH₃ | H | H | |
| 1.014 | O | C—H | 0 | HC≡CCH₂ | CH₃ | CH₃ | 3-Cl | H | |
| 1.015 | O | C—H | 0 | HC≡CCH₂ | CH₃ | CH₃ | 3-Br | H | |
| 1.016 | O | C—H | 0 | HC≡CCH₂ | CH₃ | CH₃ | 3-CN | H | |
| 1.017 | O | C—H | 0 | HC≡CCH₂ | CH₃ | CH₃ | 3-CF₃ | H | |
| 1.018 | O | C—H | 0 | HC≡CCH₂ | CH₃ | CH₃ | 3-CH₃ | H | |
| 1.019 | O | C—H | 0 | CH₂CF₃ | CH₃ | CH₃ | H | H | |
| 1.020 | O | C—H | 0 | CH₂CF₃ | CH₃ | CH₃ | 3-Cl | H | |
| 1.021 | O | C—H | 0 | CH₂CF₃ | CH₃ | CH₃ | 3-Br | H | |
| 1.022 | O | C—H | 0 | CH₂CF₃ | CH₃ | CH₃ | 3-CN | H | |
| 1.023 | O | C—H | 0 | CH₂CF₃ | CH₃ | CH₃ | 3-CF₃ | H | |
| 1.024 | O | C—H | 0 | CH₂CF₃ | CH₃ | CH₃ | 3-CH₃ | H | |
| 1.025 | O | C—H | 0 | CH₃ | CH₃ | CH₂CH₃ | H | H | 322 (M + 1) 0.82 min |
| 1.026 | O | C—H | 0 | CH₃ | CH₃ | CH₂CH₃ | 3-Cl | H | |
| 1.027 | O | C—H | 0 | CH₃ | CH₃ | CH₂CH₃ | 3-Br | H | |
| 1.028 | O | C—H | 0 | CH₃ | CH₃ | CH₂CH₃ | 3-CN | H | |
| 1.029 | O | C—H | 0 | CH₃ | CH₃ | CH₂CH₃ | 3-CF₃ | H | |
| 1.030 | O | C—H | 0 | CH₃ | CH₃ | CH₂CH₃ | 3-CH₃ | H | |
| 1.031 | O | C—H | 0 | CH₃ | CH₂CH₃ | CH₃ | H | H | |
| 1.032 | O | C—H | 0 | CH₃ | CH₂CH₃ | CH₃ | 3-Cl | H | |
| 1.033 | O | C—H | 0 | CH₃ | CH₂CH₃ | CH₃ | 3-Br | H | |
| 1.034 | O | C—H | 0 | CH₃ | CH₂CH₃ | CH₃ | 3-CN | H | |
| 1.035 | O | C—H | 0 | CH₃ | CH₂CH₃ | CH₃ | 3-CF₃ | H | |
| 1.036 | O | C—H | 0 | CH₃ | CH₂CH₃ | CH₃ | 3-CH₃ | H | |
| 1.037 | O | C—H | 0 | CH₃ | Cl | CH₃ | H | H | |
| 1.038 | O | C—H | 0 | CH₃ | Cl | CH₃ | 3-Cl | H | |
| 1.039 | O | C—H | 0 | CH₃ | Cl | CH₃ | 3-Br | H | |
| 1.040 | O | C—H | 0 | CH₃ | Cl | CH₃ | 3-CN | H | |
| 1.041 | O | C—H | 0 | CH₃ | Cl | CH₃ | 3-CF₃ | H | |
| 1.042 | O | C—H | 0 | CH₃ | Cl | CH₃ | 3-CH₃ | H | |
| 1.043 | O | C—H | 0 | CH₃ | Br | CH₃ | H | H | |
| 1.044 | O | C—H | 0 | CH₃ | Br | CH₃ | 3-Cl | H | |
| 1.045 | O | C—H | 0 | CH₃ | Br | CH₃ | 3-Br | H | |
| 1.046 | O | C—H | 0 | CH₃ | Br | CH₃ | 3-CN | H | |
| 1.047 | O | C—H | 0 | CH₃ | Br | CH₃ | 3-CF₃ | H | |
| 1.048 | O | C—H | 0 | CH₃ | Br | CH₃ | 3-CH₃ | H | |
| 1.049 | O | C—H | 0 | CH₃ | CF₃ | CH₃ | H | H | |
| 1.050 | O | C—H | 0 | CH₃ | CF₃ | CH₃ | 3-Cl | H | |
| 1.051 | O | C—H | 0 | CH₃ | CF₃ | CH₃ | 3-Br | H | |
| 1.052 | O | C—H | 0 | CH₃ | CF₃ | CH₃ | 3-CN | H | |
| 1.053 | O | C—H | 0 | CH₃ | CF₃ | CH₃ | 3-CF₃ | H | |
| 1.054 | O | C—H | 0 | CH₃ | CF3 | CH₃ | 3-CH₃ | H | |
| 1.055 | O | C—H | 0 | CH₃ | CF₂H | CH₃ | H | H | |
| 1.056 | O | C—H | 0 | CH₃ | CF₂H | CH₃ | 3-Cl | H | |

TABLE 1-continued

This table discloses compounds No. 1.001 to 1.267

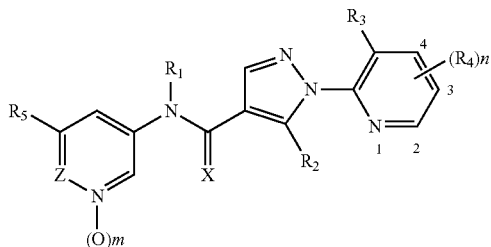
(I)

| Comp. No. | X | Z | m | R$_1$ | R$_2$ | R$_3$ | R$_4$ | R$_5$ | LCMS |
|---|---|---|---|---|---|---|---|---|---|
| 1.057 | O | C—H | 0 | CH$_3$ | CF$_2$H | CH$_3$ | 3-Br | H | |
| 1.058 | O | C—H | 0 | CH$_3$ | CF$_2$H | CH$_3$ | 3-CN | H | |
| 1.059 | O | C—H | 0 | CH$_3$ | CF$_2$H | CH$_3$ | 3-CF$_3$ | H | |
| 1.060 | O | C—H | 0 | CH$_3$ | CF$_2$H | CH$_3$ | 3-CH$_3$ | H | |
| 1.061 | S | C—H | 0 | CH$_3$ | CH$_3$ | CH$_3$ | H | H | |
| 1.062 | S | C—H | 0 | CH$_3$ | CH$_3$ | CH$_3$ | 3-Cl | H | |
| 1.063 | S | C—H | 0 | CH$_3$ | CH$_3$ | CH$_3$ | 3-Br | H | |
| 1.064 | S | C—H | 0 | CH$_3$ | CH$_3$ | CH$_3$ | 3-CN | H | |
| 1.065 | S | C—H | 0 | CH$_3$ | CH$_3$ | CH$_3$ | 3-CF$_3$ | H | |
| 1.066 | S | C—H | 0 | CH$_3$ | CH$_3$ | CH$_3$ | 3-CH$_3$ | H | |
| 1.067 | S | C—H | 0 | CH$_2$CH$_3$ | CH$_3$ | CH$_3$ | H | H | |
| 1.068 | S | C—H | 0 | CH$_2$CH$_3$ | CH$_3$ | CH$_3$ | 3-Cl | H | |
| 1.069 | S | C—H | 0 | CH$_2$CH$_3$ | CH$_3$ | CH$_3$ | 3-Br | H | |
| 1.070 | S | C—H | 0 | CH$_2$CH$_3$ | CH$_3$ | CH$_3$ | 3-CN | H | |
| 1.071 | S | C—H | 0 | CH$_2$CH$_3$ | CH$_3$ | CH$_3$ | 3-CF$_3$ | H | |
| 1.072 | S | C—H | 0 | CH$_2$CH$_3$ | CH$_3$ | CH$_3$ | 3-CH$_3$ | H | |
| 1.073 | S | C—H | 0 | CH$_3$ | CH$_3$ | CH$_2$CH$_3$ | H | H | |
| 1.074 | S | C—H | 0 | CH$_3$ | CH$_3$ | CH$_2$CH$_3$ | 3-Cl | H | |
| 1.075 | S | C—H | 0 | CH$_3$ | CH$_3$ | CH$_2$CH$_3$ | 3-Br | H | |
| 1.076 | S | C—H | 0 | CH$_3$ | CH$_3$ | CH$_2$CH$_3$ | 3-CN | H | |
| 1.077 | S | C—H | 0 | CH$_3$ | CH$_3$ | CH$_2$CH$_3$ | 3-CF$_3$ | H | |
| 1.078 | S | C—H | 0 | CH$_3$ | CH$_3$ | CH$_2$CH$_3$ | 3-CH$_3$ | H | |
| 1.079 | O | C—H | 1 | CH$_3$ | CH$_3$ | CH$_3$ | H | H | 1H NMR (CDCl$_3$, ppm): 2.20 (s, 3H), 2.31 (s, 3H), 3.49 (s, 3H), 7.13 (dd, 1H), 7.20-7.31 (m, 4H), 8.10 (d, 1H), 8.20 (d, 2H), 8.24 (m, 1H) |
| 1.080 | O | C—H | 1 | CH$_3$ | CH$_3$ | CH$_3$ | 3-Cl | H | 342/344 (M + 1) 0.72 min |
| 1.081 | O | C—H | 1 | CH$_3$ | CH$_3$ | CH$_3$ | 3-Br | H | 386/388 (M + 1) 0.76 min |
| 1.082 | O | C—H | 1 | CH$_3$ | CH$_3$ | CH$_3$ | 3-CN | H | |
| 1.083 | O | C—H | 1 | CH$_3$ | CH$_3$ | CH$_3$ | 3-CF$_3$ | H | |
| 1.084 | O | C—H | 1 | CH$_3$ | CH$_3$ | CH$_3$ | 3-CH$_3$ | H | |
| 1.085 | O | C—H | 1 | CH$_2$CH$_3$ | CH$_3$ | CH$_3$ | H | H | |
| 1.086 | O | C—H | 1 | CH$_2$CH$_3$ | CH$_3$ | CH$_3$ | 3-Cl | H | |
| 1.087 | O | C—H | 1 | CH$_2$CH$_3$ | CH$_3$ | CH$_3$ | 3-Br | H | |
| 1.088 | O | C—H | 1 | CH$_2$CH$_3$ | CH$_3$ | CH$_3$ | 3-CN | H | |
| 1.089 | O | C—H | 1 | CH$_2$CH$_3$ | CH$_3$ | CH$_3$ | 3-CF$_3$ | H | |
| 1.090 | O | C—H | 1 | CH$_2$CH$_3$ | CH$_3$ | CH$_3$ | 3-CH$_3$ | H | |
| 1.091 | O | C—H | 1 | CH$_3$ | CH$_3$ | CH$_2$CH$_3$ | H | H | |
| 1.092 | O | C—H | 1 | CH$_3$ | CH$_3$ | CH$_2$CH$_3$ | 3-Cl | H | |
| 1.093 | O | C—H | 1 | CH$_3$ | CH$_3$ | CH$_2$CH$_3$ | 3-Br | H | |
| 1.094 | O | C—H | 1 | CH$_3$ | CH$_3$ | CH$_2$CH$_3$ | 3-CN | H | |
| 1.095 | O | C—H | 1 | CH$_3$ | CH$_3$ | CH$_2$CH$_3$ | 3-CF$_3$ | H | |
| 1.096 | O | C—H | 1 | CH$_3$ | CH$_3$ | CH$_2$CH$_3$ | 3-CH$_3$ | H | |
| 1.097 | O | C—H | 0 | CH$_3$ | CH$_3$ | CH$_3$ | 2-F | H | |
| 1.098 | O | C—H | 0 | CH$_3$ | CH$_3$ | CH$_3$ | 2-Cl | H | 342/4 (M + 1) 0.71 min |
| 1.099 | O | C—H | 0 | CH$_3$ | CH$_3$ | CH$_3$ | 2-Br | H | |
| 1.100 | O | C—H | 0 | CH$_3$ | CH$_3$ | CH$_3$ | 2-CN | H | |
| 1.101 | O | C—H | 0 | CH$_3$ | CH$_3$ | CH$_3$ | 2-CF$_3$ | H | |
| 1.102 | O | C—H | 0 | CH$_3$ | CH$_3$ | CH$_3$ | 2-CH$_3$ | H | |
| 1.103 | O | C—H | 0 | CH$_2$CH$_3$ | CH$_3$ | CH$_3$ | 2-F | H | |
| 1.104 | O | C—H | 0 | CH$_2$CH$_3$ | CH$_3$ | CH$_3$ | 2-Cl | H | |
| 1.105 | O | C—H | 0 | CH$_2$CH$_3$ | CH$_3$ | CH$_3$ | 2-Br | H | |
| 1.106 | O | C—H | 0 | CH$_2$CH$_3$ | CH$_3$ | CH$_3$ | 2-CN | H | |
| 1.107 | O | C—H | 0 | CH$_2$CH$_3$ | CH$_3$ | CH$_3$ | 2-CF$_3$ | H | |
| 1.108 | O | C—H | 0 | CH$_2$CH$_3$ | CH$_3$ | CH$_3$ | 2-CH$_3$ | H | |
| 1.109 | O | C—H | 0 | CH$_3$ | CH$_3$ | CH$_2$CH$_3$ | 2-F | H | |
| 1.110 | O | C—H | 0 | CH$_3$ | CH$_3$ | CH$_2$CH$_3$ | 2-Cl | H | |
| 1.111 | O | C—H | 0 | CH$_3$ | CH$_3$ | CH$_2$CH$_3$ | 2-Br | H | |

TABLE 1-continued

This table discloses compounds No. 1.001 to 1.267

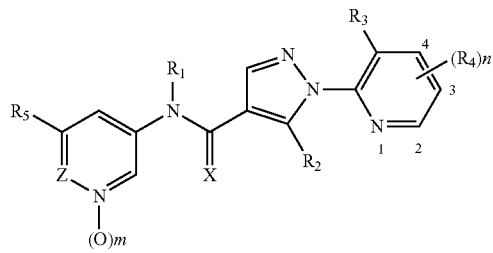

(I)

| Comp. No. | X | Z | m | $R_1$ | $R_2$ | $R_3$ | $R_4$ | $R_5$ | LCMS |
|---|---|---|---|---|---|---|---|---|---|
| 1.112 | O | C—H | 0 | $CH_3$ | $CH_3$ | $CH_2CH_3$ | 2-CN | H | |
| 1.113 | O | C—H | 0 | $CH_3$ | $CH_3$ | $CH_2CH_3$ | 2-$CF_3$ | H | |
| 1.114 | O | C—H | 0 | $CH_3$ | $CH_3$ | $CH_2CH_3$ | 2-$CH_3$ | H | |
| 1.115 | O | C—H | 0 | $CH_3$ | $CH_3$ | $CH_3$ | 4-F | H | |
| 1.116 | O | C—H | 0 | $CH_3$ | $CH_3$ | $CH_3$ | 4-Cl | H | 343/5 (M + 1) 0.70 min |
| 1.117 | O | C—H | 0 | $CH_3$ | $CH_3$ | $CH_3$ | 4-Br | H | |
| 1.118 | O | C—H | 0 | $CH_3$ | $CH_3$ | $CH_3$ | 4-CN | H | |
| 1.119 | O | C—H | 0 | $CH_3$ | $CH_3$ | $CH_3$ | 4-$CF_3$ | H | |
| 1.120 | O | C—H | 0 | $CH_3$ | $CH_3$ | $CH_3$ | 4-$CH_3$ | H | |
| 1.121 | O | C—H | 0 | $CH_2CH_3$ | $CH_3$ | $CH_3$ | 4-F | H | |
| 1.122 | O | C—H | 0 | $CH_2CH_3$ | $CH_3$ | $CH_3$ | 4-Cl | H | |
| 1.123 | O | C—H | 0 | $CH_2CH_3$ | $CH_3$ | $CH_3$ | 4-Br | H | |
| 1.124 | O | C—H | 0 | $CH_2CH_3$ | $CH_3$ | $CH_3$ | 4-CN | H | |
| 1.125 | O | C—H | 0 | $CH_2CH_3$ | $CH_3$ | $CH_3$ | 4-$CF_3$ | H | |
| 1.126 | O | C—H | 0 | $CH_2CH_3$ | $CH_3$ | $CH_3$ | 4-$CH_3$ | H | |
| 1.127 | O | C—H | 0 | $CH_3$ | $CH_3$ | $CH_2CH_3$ | 4-F | H | |
| 1.128 | O | C—H | 0 | $CH_3$ | $CH_3$ | $CH_2CH_3$ | 4-Cl | H | |
| 1.129 | O | C—H | 0 | $CH_3$ | $CH_3$ | $CH_2CH_3$ | 4-Br | H | |
| 1.130 | O | C—H | 0 | $CH_3$ | $CH_3$ | $CH_2CH_3$ | 4-CN | H | |
| 1.131 | O | C—H | 0 | $CH_3$ | $CH_3$ | $CH_2CH_3$ | 4-$CF_3$ | H | |
| 1.132 | O | C—H | 0 | $CH_3$ | $CH_3$ | $CH_2CH_3$ | 4-$CH_3$ | H | |
| 1.133 | O | N | 0 | $CH_3$ | $CH_3$ | $CH_3$ | H | H | 309 (M + 1) 0.56 min |
| 1.134 | O | N | 0 | $CH_3$ | $CH_3$ | $CH_3$ | 3-Cl | H | |
| 1.135 | O | N | 0 | $CH_3$ | $CH_3$ | $CH_3$ | 3-Br | H | |
| 1.136 | O | N | 0 | $CH_3$ | $CH_3$ | $CH_3$ | 3-CN | H | |
| 1.137 | O | N | 0 | $CH_3$ | $CH_3$ | $CH_3$ | 3-$CF_3$ | H | |
| 1.138 | O | N | 0 | $CH_3$ | $CH_3$ | $CH_3$ | 3-$CH_3$ | H | |
| 1.139 | O | N | 0 | $CH_2CH_3$ | $CH_3$ | $CH_3$ | H | H | |
| 1.140 | O | N | 0 | $CH_2CH_3$ | $CH_3$ | $CH_3$ | 3-Cl | H | |
| 1.141 | O | N | 0 | $CH_2CH_3$ | $CH_3$ | $CH_3$ | 3-Br | H | |
| 1.142 | O | N | 0 | $CH_2CH_3$ | $CH_3$ | $CH_3$ | 3-CN | H | |
| 1.143 | O | N | 0 | $CH_2CH_3$ | $CH_3$ | $CH_3$ | 3-$CF_3$ | H | |
| 1.144 | O | N | 0 | $CH_2CH_3$ | $CH_3$ | $CH_3$ | 3-$CH_3$ | H | |
| 1.145 | O | N | 0 | $HC\equiv CCH_2$ | $CH_3$ | $CH_3$ | H | H | |
| 1.146 | O | N | 0 | $HC\equiv CCH_2$ | $CH_3$ | $CH_3$ | 3-Cl | H | |
| 1.147 | O | N | 0 | $HC\equiv CCH_2$ | $CH_3$ | $CH_3$ | 3-Br | H | |
| 1.148 | O | N | 0 | $HC\equiv CCH_2$ | $CH_3$ | $CH_3$ | 3-CN | H | |
| 1.149 | O | N | 0 | $HC\equiv CCH_2$ | $CH_3$ | $CH_3$ | 3-$CF_3$ | H | |
| 1.150 | O | N | 0 | $HC\equiv CCH_2$ | $CH_3$ | $CH_3$ | 3-$CH_3$ | H | |
| 1.151 | O | N | 0 | $CH_2CF_3$ | $CH_3$ | $CH_3$ | H | H | |
| 1.152 | O | N | 0 | $CH_2CF_3$ | $CH_3$ | $CH_3$ | 3-Cl | H | |
| 1.153 | O | N | 0 | $CH_2CF_3$ | $CH_3$ | $CH_3$ | 3-Br | H | |
| 1.154 | O | N | 0 | $CH_2CF_3$ | $CH_3$ | $CH_3$ | 3-CN | H | |
| 1.155 | O | N | 0 | $CH_2CF_3$ | $CH_3$ | $CH_3$ | 3-$CF_3$ | H | |
| 1.156 | O | N | 0 | $CH_2CF_3$ | $CH_3$ | $CH_3$ | 3-$CH_3$ | H | |
| 1.157 | O | N | 0 | $CH_3$ | $CH_3$ | $CH_2CH_3$ | H | H | |
| 1.158 | O | N | 0 | $CH_3$ | $CH_3$ | $CH_2CH_3$ | 3-Cl | H | |
| 1.159 | O | N | 0 | $CH_3$ | $CH_3$ | $CH_2CH_3$ | 3-Br | H | |
| 1.160 | O | N | 0 | $CH_3$ | $CH_3$ | $CH_2CH_3$ | 3-CN | H | |
| 1.161 | O | N | 0 | $CH_3$ | $CH_3$ | $CH_2CH_3$ | 3-$CF_3$ | H | |
| 1.162 | O | N | 0 | $CH_3$ | $CH_3$ | $CH_2CH_3$ | 3-$CH_3$ | H | |
| 1.163 | O | N | 0 | $CH_3$ | $CH_2CH_3$ | $CH_3$ | H | H | |
| 1.164 | O | N | 0 | $CH_3$ | $CH_2CH_3$ | $CH_3$ | 3-Cl | H | |
| 1.165 | O | N | 0 | $CH_3$ | $CH_2CH_3$ | $CH_3$ | 3-Br | H | |
| 1.166 | O | N | 0 | $CH_3$ | $CH_2CH_3$ | $CH_3$ | 3-CN | H | |
| 1.167 | O | N | 0 | $CH_3$ | $CH_2CH_3$ | $CH_3$ | 3-$CF_3$ | H | |
| 1.168 | O | N | 0 | $CH_3$ | $CH_2CH_3$ | $CH_3$ | 3-$CH_3$ | H | |
| 1.169 | O | N | 0 | $CH_3$ | Cl | $CH_3$ | H | H | |
| 1.170 | O | N | 0 | $CH_3$ | Cl | $CH_3$ | 3-Cl | H | |

TABLE 1-continued

This table discloses compounds No. 1.001 to 1.267

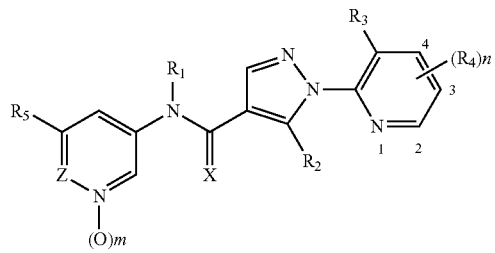

(I)

| Comp. No. | X | Z | m | R₁ | R₂ | R₃ | R₄ | R₅ | LCMS |
|---|---|---|---|---|---|---|---|---|---|
| 1.171 | O | N | 0 | CH₃ | Cl | CH₃ | 3-Br | H | |
| 1.172 | O | N | 0 | CH₃ | Cl | CH₃ | 3-CN | H | |
| 1.173 | O | N | 0 | CH₃ | Cl | CH₃ | 3-CF₃ | H | |
| 1.174 | O | N | 0 | CH₃ | Cl | CH₃ | 3-CH₃ | H | |
| 1.175 | O | N | 0 | CH₃ | Br | CH₃ | H | H | |
| 1.176 | O | N | 0 | CH₃ | Br | CH₃ | 3-Cl | H | |
| 1.177 | O | N | 0 | CH₃ | Br | CH₃ | 3-Br | H | |
| 1.178 | O | N | 0 | CH₃ | Br | CH₃ | 3-CN | H | |
| 1.179 | O | N | 0 | CH₃ | Br | CH₃ | 3-CF₃ | H | |
| 1.180 | O | N | 0 | CH₃ | Br | CH₃ | 3-CH₃ | H | |
| 1.181 | O | N | 0 | CH₃ | CF₃ | CH₃ | H | H | |
| 1.182 | O | N | 0 | CH₃ | CF₃ | CH₃ | 3-Cl | H | |
| 1.183 | O | N | 0 | CH₃ | CF₃ | CH₃ | 3-Br | H | |
| 1.184 | O | N | 0 | CH₃ | CF₃ | CH₃ | 3-CN | H | |
| 1.185 | O | N | 0 | CH₃ | CF₃ | CH₃ | 3-CF₃ | H | |
| 1.186 | O | N | 0 | CH₃ | CF₃ | CH₃ | 3-CH₃ | H | |
| 1.187 | O | N | 0 | CH₃ | CF₂H | CH₃ | H | H | |
| 1.188 | O | N | 0 | CH₃ | CF₂H | CH₃ | 3-Cl | H | |
| 1.189 | O | N | 0 | CH₃ | CF₂H | CH₃ | 3-Br | H | |
| 1.190 | O | N | 0 | CH₃ | CF₂H | CH₃ | 3-CN | H | |
| 1.191 | O | N | 0 | CH₃ | CF₂H | CH₃ | 3-CF₃ | H | |
| 1.192 | O | N | 0 | CH₃ | CF₂H | CH₃ | 3-CH₃ | H | |
| 1.193 | S | N | 0 | CH₃ | CH₃ | CH₃ | H | H | |
| 1.194 | S | N | 0 | CH₃ | CH₃ | CH₃ | 3-Cl | H | |
| 1.195 | S | N | 0 | CH₃ | CH₃ | CH₃ | 3-Br | H | |
| 1.196 | S | N | 0 | CH₃ | CH₃ | CH₃ | 3-CN | H | |
| 1.197 | S | N | 0 | CH₃ | CH₃ | CH₃ | 3-CF₃ | H | |
| 1.198 | S | N | 0 | CH₃ | CH₃ | CH₃ | 3-CH₃ | H | |
| 1.199 | S | N | 0 | CH₂CH₃ | CH₃ | CH₃ | H | H | |
| 1.200 | S | N | 0 | CH₂CH₃ | CH₃ | CH₃ | 3-Cl | H | |
| 1.201 | S | N | 0 | CH₂CH₃ | CH₃ | CH₃ | 3-Br | H | |
| 1.202 | S | N | 0 | CH₂CH₃ | CH₃ | CH₃ | 3-CN | H | |
| 1.203 | S | N | 0 | CH₂CH₃ | CH₃ | CH₃ | 3-CF₃ | H | |
| 1.204 | S | N | 0 | CH₂CH₃ | CH₃ | CH₃ | 3-CH₃ | H | |
| 1.205 | S | N | 0 | CH₃ | CH₃ | CH₂CH₃ | H | H | |
| 1.206 | S | N | 0 | CH₃ | CH₃ | CH₂CH₃ | 3-Cl | H | |
| 1.207 | S | N | 0 | CH₃ | CH₃ | CH₂CH₃ | 3-Br | H | |
| 1.208 | S | N | 0 | CH₃ | CH₃ | CH₂CH₃ | 3-CN | H | |
| 1.209 | S | N | 0 | CH₃ | CH₃ | CH₂CH₃ | 3-CF₃ | H | |
| 1.210 | S | N | 0 | CH₃ | CH₃ | CH₂CH₃ | 3-CH₃ | H | |
| 1.211 | O | N | 1 | CH₃ | CH₃ | CH₃ | H | H | |
| 1.212 | O | N | 1 | CH₃ | CH₃ | CH₃ | 3-Cl | H | |
| 1.213 | O | N | 1 | CH₃ | CH₃ | CH₃ | 3-Br | H | |
| 1.214 | O | N | 1 | CH₃ | CH₃ | CH₃ | 3-CN | H | |
| 1.215 | O | N | 1 | CH₃ | CH₃ | CH₃ | 3-CF₃ | H | |
| 1.216 | O | N | 1 | CH₃ | CH₃ | CH₃ | 3-CH₃ | H | |
| 1.217 | O | N | 1 | CH₂CH₃ | CH₃ | CH₃ | H | H | |
| 1.218 | O | N | 1 | CH₂CH₃ | CH₃ | CH₃ | 3-Cl | H | |
| 1.219 | O | N | 1 | CH₂CH₃ | CH₃ | CH₃ | 3-Br | H | |
| 1.220 | O | N | 1 | CH₂CH₃ | CH₃ | CH₃ | 3-CN | H | |
| 1.221 | O | N | 1 | CH₂CH₃ | CH₃ | CH₃ | 3-CF₃ | H | |
| 1.222 | O | N | 1 | CH₂CH₃ | CH₃ | CH₃ | 3-CH₃ | H | |
| 1.223 | O | N | 1 | CH₃ | CH₃ | CH₂CH₃ | H | H | |
| 1.224 | O | N | 1 | CH₃ | CH₃ | CH₂CH₃ | 3-Cl | H | |
| 1.225 | O | N | 1 | CH₃ | CH₃ | CH₂CH₃ | 3-Br | H | |
| 1.226 | O | N | 1 | CH₃ | CH₃ | CH₂CH₃ | 3-CN | H | |
| 1.227 | O | N | 1 | CH₃ | CH₃ | CH₂CH₃ | 3-CF₃ | H | |
| 1.228 | O | N | 1 | CH₃ | CH₃ | CH₂CH₃ | 3-CH₃ | H | |
| 1.229 | O | N | 0 | CH₃ | CH₃ | CH₃ | 2-F | H | |

TABLE 1-continued

This table discloses compounds No. 1.001 to 1.267

(I)

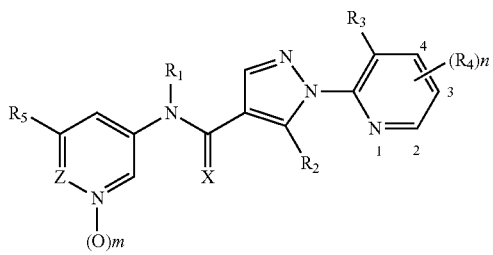

| Comp. No. | X | Z | m | $R_1$ | $R_2$ | $R_3$ | $R_4$ | $R_5$ | LCMS |
|---|---|---|---|---|---|---|---|---|---|
| 1.230 | O | N | 0 | $CH_3$ | $CH_3$ | $CH_3$ | 2-Cl | H | 343/5 (M + 1) 0.69 min mp: 190-4° C. |
| 1.231 | O | N | 0 | $CH_3$ | $CH_3$ | $CH_3$ | 2-Br | H | |
| 1.232 | O | N | 0 | $CH_3$ | $CH_3$ | $CH_3$ | 2-CN | H | |
| 1.233 | O | N | 0 | $CH_3$ | $CH_3$ | $CH_3$ | 2-$CF_3$ | H | |
| 1.234 | O | N | 0 | $CH_3$ | $CH_3$ | $CH_3$ | 2-$CH_3$ | H | |
| 1.235 | O | N | 0 | $CH_2CH_3$ | $CH_3$ | $CH_3$ | 2-F | H | |
| 1.236 | O | N | 0 | $CH_2CH_3$ | $CH_3$ | $CH_3$ | 2-Cl | H | |
| 1.237 | O | N | 0 | $CH_2CH_3$ | $CH_3$ | $CH_3$ | 2-Br | H | |
| 1.238 | O | N | 0 | $CH_2CH_3$ | $CH_3$ | $CH_3$ | 2-CN | H | |
| 1.239 | O | N | 0 | $CH_2CH_3$ | $CH_3$ | $CH_3$ | 2-$CF_3$ | H | |
| 1.240 | O | N | 0 | $CH_2CH_3$ | $CH_3$ | $CH_3$ | 2-$CH_3$ | H | |
| 1.241 | O | N | 0 | $CH_3$ | $CH_3$ | $CH_2CH_3$ | 2-F | H | |
| 1.242 | O | N | 0 | $CH_3$ | $CH_3$ | $CH_2CH_3$ | 2-Cl | H | |
| 1.243 | O | N | 0 | $CH_3$ | $CH_3$ | $CH_2CH_3$ | 2-Br | H | |
| 1.244 | O | N | 0 | $CH_3$ | $CH_3$ | $CH_2CH_3$ | 2-CN | H | |
| 1.245 | O | N | 0 | $CH_3$ | $CH_3$ | $CH_2CH_3$ | 2-$CF_3$ | H | |
| 1.246 | O | N | 0 | $CH_3$ | $CH_3$ | $CH_2CH_3$ | 2-$CH_3$ | H | |
| 1.247 | O | N | 0 | $CH_3$ | $CH_3$ | $CH_3$ | 4-F | H | |
| 1.248 | O | N | 0 | $CH_3$ | $CH_3$ | $CH_3$ | 4-Cl | H | 343/5 (M + 1) 0.69 min mp: 185-9° C. |
| 1.249 | O | N | 0 | $CH_3$ | $CH_3$ | $CH_3$ | 4-Br | H | |
| 1.250 | O | N | 0 | $CH_3$ | $CH_3$ | $CH_3$ | 4-CN | H | |
| 1.251 | O | N | 0 | $CH_3$ | $CH_3$ | $CH_3$ | 4-$CF_3$ | H | |
| 1.252 | O | N | 0 | $CH_3$ | $CH_3$ | $CH_3$ | 4-$CH_3$ | H | |
| 1.253 | O | N | 0 | $CH_2CH_3$ | $CH_3$ | $CH_3$ | 4-F | H | |
| 1.254 | O | N | 0 | $CH_2CH_3$ | $CH_3$ | $CH_3$ | 4-Cl | H | |
| 1.255 | O | N | 0 | $CH_2CH_3$ | $CH_3$ | $CH_3$ | 4-Br | H | |
| 1.256 | O | N | 0 | $CH_2CH_3$ | $CH_3$ | $CH_3$ | 4-CN | H | |
| 1.257 | O | N | 0 | $CH_2CH_3$ | $CH_3$ | $CH_3$ | 4-$CF_3$ | H | |
| 1.258 | O | N | 0 | $CH_2CH_3$ | $CH_3$ | $CH_3$ | 4-$CH_3$ | H | |
| 1.259 | O | N | 0 | $CH_3$ | $CH_3$ | $CH_2CH_3$ | 4-F | H | |
| 1.260 | O | N | 0 | $CH_3$ | $CH_3$ | $CH_2CH_3$ | 4-Cl | H | |
| 1.261 | O | N | 0 | $CH_3$ | $CH_3$ | $CH_2CH_3$ | 4-Br | H | |
| 1.262 | O | N | 0 | $CH_3$ | $CH_3$ | $CH_2CH_3$ | 4-CN | H | |
| 1.263 | O | N | 0 | $CH_3$ | $CH_3$ | $CH_2CH_3$ | 4-$CF_3$ | H | |
| 1.264 | O | N | 0 | $CH_3$ | $CH_3$ | $CH_2CH_3$ | 4-$CH_3$ | H | |
| 1.265 | O | C—H | 0 | $CH_3$ | $CH_3$ | $CH_3$ | H | F | |
| 1.266 | O | C—H | 0 | $CH_3$ | $CH_3$ | $CH_3$ | H | Cl | |
| 1.267 | O | C—H | 0 | $CH_3$ | $CH_3$ | $CH_3$ | H | Br | |

Formulation Examples (%=Percent by Weight)

Example F1

| | Emulsion concentrates | | |
|---|---|---|---|
| | a) | b) | c) |
| Active ingredient | 25% | 40% | 50% |
| Calcium dodecylbenzenesulfonate | 5% | 8% | 6% |
| Castor oil polyethylene glycol ether (36 mol of EO) | 5% | — | — |
| Tributylphenoxypolyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

Example F2

| | Solutions | | | |
|---|---|---|---|---|
| | a) | b) | c) | d) |
| Active ingredient | 80% | 10% | 5% | 95% |
| Ethylene glycol monomethyl ether | 20% | — | — | — |
| Polyethylene glycol MW 400 | — | 70% | — | — |
| N-Methylpyrrolid-2-one | — | 20% | — | — |
| Epoxidized coconut oil | — | — | 1% | 5% |
| Petroleum ether (boiling range: 160-190°) | — | — | 94% | — |

The solutions are suitable for use in the form of microdrops.

Example F3

| | Granules | | | |
|---|---|---|---|---|
| | a) | b) | c) | d) |
| Active ingredient | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredient is dissolved in dichloromethane, the solution is sprayed onto the carrier(s), and the solvent is subsequently evaporated in vacuo.

Example F4

| | Dusts | |
|---|---|---|
| | a) | b) |
| Active ingredient | 2% | 5% |
| Highly disperse silica | 1% | 5% |
| Talc | 97% | — |
| Kaolin | — | 90% |

Ready-to-use dusts are obtained by intimately mixing the carriers and the active ingredient.

Example F5

| | Wettable powders | | |
|---|---|---|---|
| | a) | b) | c) |
| Active ingredient | 25% | 50% | 75% |
| Sodium lignosulfonate | 5% | 5% | — |
| Sodium lauryl sulfate | 3% | — | 5% |
| Sodium diisobutyl-naphthalenesulfonate | — | 6% | 10% |
| Octylphenoxypolyethylene glycol ether (7-8 mol of EO) | — | 2% | — |
| Highly disperse silica | 5% | 10% | 10% |
| Kaolin | 62% | 27% | — |

The active ingredient is mixed with the additives and the mixture is ground thoroughly in a suitable mill. This gives wettable powders, which can be diluted with water to give suspensions of any desired concentration.

Example F6

| Extruder granules | |
|---|---|
| Active ingredient | 10% |
| Sodium lignosulfonate | 2% |
| Carboxymethylcellulose | 1% |
| Kaolin | 87% |

The active ingredient is mixed with the additives, and the mixture is ground, moistened with water, extruded, granulated and dried in a stream of air.

Example F7

| Coated granules | |
|---|---|
| Active ingredient | 3% |
| Polyethylene glycol (MW 200) | 3% |
| Kaolin | 94% |

In a mixer, the finely ground active ingredient is applied uniformly to the kaolin, which has been moistened with the polyethylene glycol. This gives dust-free coated granules.

Example F8

| Suspension concentrate | |
|---|---|
| Active ingredient | 40% |
| Ethylene glycol | 10% |
| Nonylphenoxypolyethylene glycol ether (15 mol of EO) | 6% |
| Sodium lignosulfonate | 10% |
| Carboxymethylcellulose | 1% |
| 37% aqueous formaldehyde solution | 0.2% |
| Silicone oil (75% aqueous emulsion) | 0.8% |
| Water | 32% |

The finely ground active ingredient is mixed intimately with the additives. Suspensions of any desired concentration can be prepared from the thus resulting suspension concentrate by dilution with water.

Example F9: Dustable Powder Application (DS) on Barley Seeds

1. Preparation of the DS Blank Formulation

In order to treat the barley seed, the active ingredient had to be homogeneously distributed on an adsorptive material: a carrier material was prepared by mixing a urea based polymer with formaldehyde (eg. Pergopak M) and an aluminium silicate (eg. Kaolin Powder AG), followed by an air jet milling procedure to achieve median particle size of approx. 2-5 μm (CILAS 420 particle sizer; measured in aqueous dispersion using a surfactant).

The following compositions were used for the different blank formulations:

DS60 Blank Formulation:

| conc. | Ingredient Name | Supplier |
|---|---|---|
| 5% w/w | Pergopak M | Albermale corporation |
| 95% w/w | Kaolin Powder AG | Argirec |

DS25 Blank Formulation:

| conc. | Ingredient Name | Supplier |
|---|---|---|
| 47.37% w/w | Pergopak M | Albermale corporation |
| 52.63% w/w | Kaolin Powder AG | Argirec |

DS5 Blank Formulation:

| conc. | Ingredient Name | Supplier |
|---|---|---|
| 33.33% w/w | Pergopak M | Albermale corporation |
| 66.67% w/w | Kaolin Powder AG | Argirec |

2. Preparation of the DS Formulation for Application Onto the Seeds

When the active ingredient showed a liquid character, it had to be dissolved in acetone before it was mixed with the corresponding amount of the above mentioned DS blank formulation. The solution was then transferred into a porcelain mortar vessel and heated up to 40-50° C. to evaporate the solvent in the air stream of the fume cupboard.

To ensure enough material is present later for application, the ratio of carrier had to be adjusted to the needed seed loading rate. (ie. for low dose treatments, a lower concentrated DS formulation was used, to be able to handle a bigger volume of material).

After evaporation of the solvent, the residual active ingredient was found precipitated on the carrier particles, either adsorbed as a film (for liquid active ingredients) or as crystals (for solid active ingredients).

This mixture was then scratched off from the bottom of the mortar vessel with a spatula and gently grinded with a pistil to form an homogenous powder.

3. Preparation of a Sticking Polymer 40 g of a sticking polymer (eg. Vinamul 18160) was put in a polyethylene flask and diluted with 60 g of water. The bottle was shaken to homogenize the solution.

4. Application of the Barley Seed

Barley seeds were put into a 50 ml flat bottom glass flask. Two to three droplets of sticking polymer were added to the bottom of the glass without hitting any seed directly. The seeds were then stirred with a spatula to allow them to get covered as homogenously as possible with the sticking polymer. During this step, some seeds may start to stick together or stick to the glass vessel. Stirring was continued until the seeds just started to separate again and flowed mostly free. The seeds were transferred into an Erlenmeyer flat bottom flask which was already containing the required amount of DS formulation, evenly distributed at the bottom of the vessel. The Erlenmeyer flask was shaken in a way that the seeds tumbled around on its bottom. During this process, the DS formulation was continuously collected from the flask surface by the sticky seeds.

The following table shows the amounts of active ingredients and of formulations needed for 5 treatments of 15 seeds at different seed loading rates.

| Target mg ai/seed | ai. needed mg per treatment | formulation mg per treatment | conc. of ai. in formulation | ai. needed mg per formulation | factor to compensate prep. losses | ai. needed mg per prep. | blank needed mg per prep. |
|---|---|---|---|---|---|---|---|
| 1 | 15 | 25 | 60% | 19.5 for DS60 | ×1.5 | 29.25 | 19.50 |
| 0.3 | 4.50 | 7.50 | 60% | | | | |
| 0.1 | 1.50 | 6.00 | 25% | 1.5 for DS25 | ×1.5 | 2.25 | 6.75 |
| 0.03 | 0.45 | 9.00 | 5% | 0.6 for DS5 | ×1.5 | 0.90 | 17.10 |
| 0.01 | 0.15 | 3.00 | 5% | | | | |

For example, for the treatment of 15 seeds at 0.1 mg per seed load rate, a DS25 formulation was used, where 2.25 mg of the active ingredient were dissolved in acetone and mixed with 6.75 mg blank formulation. After evaporation of acetone and grinding as described above, 6.00 mg of the resulting formulation were taken for treatment.

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use. Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds described in Table 1 of the present invention"):

an adjuvant selected from the group of substances consisting of petroleum oils (alternative name) (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IU- PAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IU- PAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056),+TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IU- PAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxy-aminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl 0-ethyl ethylphosphonothioate (IUPAC name) (1057)+TX, 0,0-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]30 TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3][112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzo-lar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-L190 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon

[57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (dislosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H,11Hnaphtho[2, 1-b]pyrano[3,4-e]pyran-4-yl]methyl-cyclopropanecarboxylate [915972-17-7]+TX and 1,3,5-trimethyl-N-(2-methyl-1-oxopropyl)-N-[3-(2-methylpropyl)-4-[2,2,2-trifluoro-1-methoxy-1-(trifluoromethyl)ethyl]phenyl]-1H-pyrazole-4-carboxamide [926914-55-8]+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "develoment code" is used or, if neither one of those designations nor a "common name" is used, an "alternative name" is employed. "CAS Reg. No" means the Chemical Abstracts Registry Number.

The active ingredient mixture of the compounds of formula I selected from Table 1 with active ingredients described above comprises a compound selected from Table 1 and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from Table 1 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Table 1 and the active ingredients as described above is not essential for working the present invention.

Biological Examples

These examples illustrate the pesticidal/insecticidal properties of compounds of formula I.

Example B1: Activity Against *Myzus persicae* (Green Peach Aphid) (Mixed Population, Feeding/Residual Contact Activity, Preventive)

Sunflower leaf discs were placed on agar in a 24-well microtiter plate and sprayed with test solutions. After drying, the leaf discs were infested with an aphid population of mixed ages. After an incubation period of 6 days, samples were checked for mortality and special effects (e.g. phytotoxicity). In this test, compounds 1.001, 1.002, 1.003, 1.004, 1.007, 1.025, 1.079, 1.080, 1.081, 1.098, 1.116, 1.133, 1.230 and 1.248 showed an activity of equal to or larger than 80% at a concentration of 200 ppm.

Example B2: Activity Against *Myzus persicae* (Green Peach Aphid) (Mixed Population, Systemic/Feeding Activity, Curative)

Pea seedlings, infested with an aphid population of mixed ages, were placed with the roots directly in the test solutions. 6 days after introduction, samples were checked for mortality and special effects on the plant.

In this test, compounds 1.001, 1.004, 1.007, 1.079, 1.098, 1.116 and 1.133 showed an activity of over 80% at a concentration of 24 ppm.

Example B3: Activity Against *Bemisia tabaci*, (Adults on Cotton, Contact, Preventative)

Cotton leaf discs are placed on agar in a 24-well microtiter plate and sprayed with test solutions. After drying, the leaf discs are infested with adult white flies. After an incubation period of 7 DAT, samples are checked for mortality and special effects (e.g. phytotoxicity).

In this test, compound 1.001, 1.007, 1.098, 1.133, 1.230 and 1.248 showed an activity of over 80% at a concentration of 200 ppm.

Example B4: Activity Against *Aphis craccivora* (Cowpea Aphid, Sugarbeet, Seed Treatment)

Sugarbeet seeds are treated with test compounds at various rates (mg a.i./seed). The seeds are sown into pots filled with soil. After placing the seeds on the soil surface they are further covered with soil. Before and during the bioassays, the plants are grown under optimal greenhouse conditions. After 14 days, the plants are infested with cowpea aphid (*Aphis craccivora*) by placing one infested pea seedling containing approximately 150 aphids of a population of mixed developmental stages onto each plant. Seven days after infestation, the number of aphids is counted per plant. Each treatment group is replicated 10 times. Each replicate contains 1 plant.

In this test, compounds 1.001, 1.004 and 1.133 showed an efficacy of over 80% in the reduction of aphids compared to the untreated control plants at a rate of 0.3 mg a.i./seed.

Example B5: Activity Against *Rhopalosiphum padi* (Bird Cherry Oat Aphid, Barley) (Seed Treatment) Mixed Population, Systemic/Feeding Activity, Preventive The barley seeds were coated with the active ingredients as described in the formulation example F9 above.

A treated barley seed was sown in a 350 ml pot filled with soil. Two weeks after sowing the barley seedling was infested with an aphid population of mixed stages. After an incubation period of seven days the grade of efficacy was estimated and expressed in percentage.

In this test, compounds 1.001, 1.004, 1.007, 1.098 and 1.116 showed an efficacy of over 80% in the reduction of aphids compared to the untreated control plants at a rate of 0.3 mg a.i./seed.

Comparative Example

Comparison of the insecticidal activity of a compound according to the invention with the structurally closest compound described in the prior art (described as compound No. 877 in Table 2 on page 87 of WO 2010/112177):

Compound 1.001
according to the invention

Compound 877
according to the prior art

Activity against *Rhopalosiphum padi* (Bird Cherry Oat Aphid, barley) (seed treatment) mixed population, systemic/feeding activity, preventive:

The barley seeds were coated with the active ingredients as described in the formulation example F9 above.

A treated barley seed was sown in a 350 ml pot filled with soil. Two weeks after sowing the barley seedling was infested with an aphid population of mixed stages. After an incubation period of seven days the grade of efficacy was estimated and expressed in percentage.

TABLE 3

| | Concentration (mg ai/seed) | Mortality (%) |
|---|---|---|
| Compound 1.001 | 1 | 99 |
| | 0.3 | 99 |
| | 0.1 | 95 |
| | 0.03 | 85 |
| | 0.01 | 70 |
| Compound 877 | 1 | 84 |
| | 0.3 | 63 |
| | 0.1 | 42 |
| | 0.03 | 0 |
| | 0.01 | 0 |

Table 3 shows that compound 1.001 according to the invention shows a substancially better insecticidal activity against *Rhopalosiphum padi* than the compound of the prior art. This enhanced effect was not to be expected on the basis of the structural similarity of these compounds.

What is claimed is:
1. A compound of formula I wherein,
m is 0 or 1;
Z is methine or nitrogen;
X is oxygen or sulfur,
$R_1$ is $C_1$-$C_6$-alkyl, halo-$C_1$-$C_6$-alkyl, $C_3$-$C_6$-cycloalkyl or $C_2$-$C_6$-alkynyl;
$R_2$ is $C_1$-$C_6$-alkyl, $C_1$-$C_6$-haloalkyl, $C_3$-$C_6$-cycloalkyl, halo-$C_3$-$C_6$-cycloalkyl, fluoro, chloro or bromo;
$R_3$ is $C_1$-$C_3$-alkyl;
$R_4$ is hydrogen, $C_1$-$C_6$-alkyl, fluoro, chloro, bromo or cyano;
n is 0, 1, 2 or 3;
$R_5$ is hydrogen, fluoro, chloro or bromo;
or an agrochemically acceptable salt thereof.
2. A compound of formula I according to claim 1, wherein Z is methine.
3. A compound of formula I according to claim 1, wherein Z is nitrogen.
4. A compound of formula I according to claim 1, wherein $R_1$ is methyl, ethyl, isopropyl, cyclopropyl, $CH_2CF_3$, or prop-2-ynyl.
5. A compound of formula I according to claim 1, wherein $R_2$ is methyl, ethyl, isopropyl, cyclopropyl, $CF_3$, $CF_2H$ or chloro.
6. A compound of formula I according to claim 1, wherein $R_3$ is methyl, ethyl or isopropyl.

7. A compound of formula I according to claim 1, wherein
m is 0;
Z is methine;
X is oxygen;
$R_1$ is methyl, ethyl, isopropyl, cyclopropyl, $CH_2CF_3$, or prop-2-ynyl;
$R_2$ is methyl, ethyl, isopropyl, cyclopropyl, $CF_3$, $CF_2H$ or chloro; and
$R_3$ is methyl, ethyl or isopropyl.

8. A compound of formula I according to claim 1, wherein
m is 0;
Z is nitrogen;
X is oxygen;
$R_1$ is methyl, ethyl, isopropyl, cyclopropyl, $CH_2CF_3$, or prop-2-ynyl;
$R_2$ is methyl, ethyl, isopropyl, cyclopropyl, $CF_3$, $CF_2H$ or chloro; and
$R_3$ is methyl, ethyl or isopropyl.

9. A compound of formula I according to claim 1, wherein
m is 0;
Z is methine;
X is oxygen;
$R_1$ is methyl, ethyl or prop-2-ynyl,
$R_2$ is methyl, ethyl or isopropyl, and
$R_3$ is methyl, ethyl or isopropyl.

10. A compound of formula I according to claim 1, wherein
m is 1;
Z is CH;
X is oxygen;
$R_1$ is methyl, ethyl, isopropyl, cyclopropyl, $CH_2CF_3$, or prop-2-ynyl;
$R_2$ is methyl, ethyl, isopropyl, cyclopropyl, $CF_3$, $CF_2H$ or chloro; and
$R_3$ is methyl, ethyl or isopropyl.

11. An insecticidal, acaricidal, nematicidal or molluscicidal composition, comprising an insecticidally, acaricidally, nematicidally or molluscicidally effective amount of a compound of formula I according to claim 1 and a suitable carrier or diluent therefor.

12. A method of combating and controlling pests which comprises applying an insecticidally, acaricidally, nematicidally or molluscicidally effective amount of a compound of formula I according to claim 1 or a composition comprising a compound of formula I, to a pest, a locus of pest, or to a plant susceptible to attack by a pest, with the exception of a method for treatment of the human or animal body by surgery or therapy and diagnostic methods practised on the human or animal body.

13. A method for the protection of plant propagation material from the attack by pests, which comprises treating the propagation material or the site, where the propagation material is planted, with a composition according to claim 11.

14. Plant propagation material comprising the compound of formula I according to claim 1.

* * * * *